(12) United States Patent
Iwase et al.

(10) Patent No.: US 12,263,847 B2
(45) Date of Patent: Apr. 1, 2025

(54) DRIVER ABNORMALITY DETERMINATION APPARATUS, METHOD AND COMPUTER PROGRAM

(71) Applicant: Mazda Motor Corporation, Hiroshima (JP)

(72) Inventors: Koji Iwase, Aki-gun (JP); Makoto Yoshida, Aki-gun (JP); Junichiro Kuwahara, Aki-gun (JP); Yohei Iwashita, Aki-gun (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 989 days.

(21) Appl. No.: 17/198,271

(22) Filed: Mar. 11, 2021

(65) Prior Publication Data

US 2021/0316737 A1  Oct. 14, 2021

(30) Foreign Application Priority Data

Apr. 13, 2020 (JP) .................................. 2020-071671

(51) Int. Cl.
*B60W 40/09* (2012.01)
*A61B 5/00* (2006.01)
(Continued)

(52) U.S. Cl.
CPC ........... *B60W 40/09* (2013.01); *A61B 5/1124* (2013.01); *A61B 5/163* (2017.08); *A61B 5/18* (2013.01);
(Continued)

(58) Field of Classification Search
CPC ............. B60W 40/09; B60W 50/0097; B60W 2540/10; B60W 2540/18;
(Continued)

(56) References Cited

U.S. PATENT DOCUMENTS

| 2009/0033501 | A1* | 2/2009 | Chen ........................ A61B 5/18 340/576 |
| 2010/0214087 | A1* | 8/2010 | Nakagoshi ............ B60W 40/09 340/436 |

(Continued)

FOREIGN PATENT DOCUMENTS

| JP | 2010-128649 A | 6/2010 |
| JP | 2019-79328 A | 5/2019 |
| JP | 2019-119373 A | 7/2019 |

*Primary Examiner* — Ryan W Sherwin
(74) *Attorney, Agent, or Firm* — XSENSUS LLP

(57) ABSTRACT

A driver abnormality determination apparatus includes circuitry configured to detect a driver state of a driver of a vehicle, detect a driving operation of the driver, detect an exertion level of an involuntary function of the driver based on the driver state, detect an exertion level of a driving function of the driver based on the driving operation; and determine driver abnormality based on the execution level of the involuntary function and the execution level of the driving function. On condition that a function level of one of the execution level of the involuntary function and the execution level of the driving function is equal to or lower than a specified determination criterion, the circuitry is configured to relax a determination criterion for the other function level.

9 Claims, 26 Drawing Sheets

(51) Int. Cl.
*A61B 5/11* (2006.01)
*A61B 5/16* (2006.01)
*A61B 5/18* (2006.01)
*B60W 50/00* (2006.01)

(52) U.S. Cl.
CPC ....... *A61B 5/4035* (2013.01); *B60W 50/0097* (2013.01); *B60W 2540/10* (2013.01); *B60W 2540/18* (2013.01); *B60W 2540/223* (2020.02); *B60W 2540/225* (2020.02); *B60W 2540/229* (2020.02)

(58) Field of Classification Search
CPC ..... B60W 2540/223; B60W 2540/225; B60W 2540/229; B60W 60/0059; B60W 60/0051; A61B 5/1124; A61B 5/163; A61B 5/18; A61B 5/4035; A61B 5/02055; A61B 5/7246; A61B 5/1128; A61B 5/7282; A61B 5/1114
See application file for complete search history.

(56) References Cited

U.S. PATENT DOCUMENTS

| | | | |
|---|---|---|---|
| 2012/0212353 A1* | 8/2012 | Fung | G08G 1/167 701/1 |
| 2014/0091916 A1* | 4/2014 | Aoki | B60K 28/066 340/435 |
| 2016/0001781 A1* | 1/2016 | Fung | G07C 9/37 701/36 |
| 2017/0161575 A1* | 6/2017 | Banno | A61B 5/163 |
| 2017/0311865 A1* | 11/2017 | Okuya | A61B 5/6893 |
| 2021/0016805 A1* | 1/2021 | Oba | A61B 5/18 |

\* cited by examiner

FIG. 6A

| LARGE CATEGORY | MIDDLE CATEGORY | SMALL CATEGORY | PEDAL MODEL | | | | STEER MODEL | | | RISK PREDICTION MODEL | | | ROAD SHAPE PREDICTION MODEL | |
|---|---|---|---|---|---|---|---|---|---|---|---|---|---|---|
| | | | FB GAIN | DELAY | CONTROL PERFORMANCE | ESTIMATION ERROR | FB GAIN | TRAVEL POSITION | ESTIMATION ERROR | MAGNITUDE OF POTENTIAL RISK | MAGNITUDE OF VISIBLE RISK | DEVIATION FROM LOW-RISK STATE | PREDICTION CONTROL IN LATERAL DIRECTION | PREDICTION CONTROL IN VERTICAL DIRECTION |
| PREDICTIVE FUNCTION (HIGH-ORDER FUNCTION) | RISK PREDICTIVE FUNCTION | POTENTIAL RISK | | | | | | | | ○ | | ○ | | ○ |
| | | APPROACH TO VISIBLE RISK | | | | | | | | | ○ | ○ | | ○ |
| | | ROAD SHAPE | | | | | | | | | | ○ | ○ | |
| | ATTENTION FUNCTION | CONCENTRATION | | | | | | | | ○ | ○ | ○ | ○ | ○ |
| | | ALLOCATION | | | | | | | | ○ | ○ | ○ | ○ | ○ |
| | | SPATIAL | | | | | | | | | ○ | | ○ | |
| BASE FUNCTION (LOW-ORDER FUNCTION) | PERCEPTUAL FUNCTION | LATERAL DIRECTION | ○ | | | | ○ | | ○ | | | | | |
| | | VERTICAL DIRECTION | | ○ | ○ | ○ | | | ○ | | | | | |
| | MOTOR FUNCTION | HAND | | | | | | ○ | | | | | | |
| | | FOOT | ○ | ○ | ○ | ○ | | | | | | | | |
| INVOLUNTARY FUNCTION | MOTOR FUNCTION | HAND | | | | | ○ | | | | | | | |
| | | LEFT FOOT | | | | | | | | | | | | |

FIG. 6B

| DRIVING FUNCTION | | | INDEX | | | | | | | | | | | | | |
|---|---|---|---|---|---|---|---|---|---|---|---|---|---|---|---|---|
| | | | SIGHTLINE | | | | | | | | | PUPIL DIAMETER | HEAD | | | OTHER |
| | | | POINT TO BE LOOKED AT + SIGHTLINE | SIGHTLINE | | | | | | | | | HOMEOSTASIS (POSTURE KEEPING FUNCTION) | | | |
| LARGE CATEGORY | MIDDLE CATEGORY | SMALL CATEGORY | MATCHING DEGREE BETWEEN POINT TO BE LOOKED AT AND SIGHTLINE | SALIENCY AUC | SACCADE AMPLITUDE | SACCADE FREQUENCY | SACCADE BILATERAL DIFFERENCE | SACCADE SPEED | SIGHTLINE DISTRIBUTION | MICRO-SACCADE | CYCLO-DUCTION | NYSTAGMUS | TEMPORAL CHANGE | AUTO-CORRELATION OF HEAD BEHAVIOR | CROSS-CORRELATION BETWEEN HEAD BEHAVIOR AND EXTERNAL FORCE | CROSS-CORRELATION BETWEEN HEAD BEHAVIOR AND SIGHTLINE | CROSS-CORRELATION WITH HAND/FOOT FUNCTION | ECCENTRICITY OF HEAD POSITION |
| PREDICTIVE FUNCTION (HIGH-ORDER FUNCTION) | RISK PREDICTIVE FUNCTION | VISIBLE RISK | ○ | ○ | ○ | | | | | | | | | | | | | |
| | | POTENTIAL RISK | | ○ | | ○ | | | | | | | | | | | | ○ |
| | ATTENTION FUNCTION | ATTENTION ALLOCATION (TOP-DOWN & BOTTOM-UP) | ○ | | | | | | | | | | | | | | | ○ |
| | | ATTENTION ALLOCATION (BOTTOM-UP) | ○ | ○ | | ○ | | | | | | | | | | | | |
| BASE FUNCTION (LOW-ORDER FUNCTION) | PERCEPTUAL FUNCTION | RANGE OF VISION | | | | | | | | | | | | | | | | |
| | | COGNITIVE RESPONSE TIME | | | | | ○ | | ○ | | | ○ | | | | | | |
| | MOTOR FUNCTION | MOTION OF EYEBALLS | | | | | | ○ | | | | | | | | | | |
| | | HAND-FOOT | | | | | | | | | | | | | | | ○ | |
| INVOLUNTARY FUNCTION | VESTIBULAR FUNCTION | VESTIBULO-OCULAR REFLEX | | | | | | | | | | | | | ○ | ○ | | |
| | | VESTIBULAR REFLEX | | | | | | | | | | | | | | ○ | | |
| | MOTOR FUNCTION | MOTION OF EYEBALLS | | | | | | | | ○ | | | | | | ○ | | |
| | | PUPILLARY REFLEX | | | | | | | | | ○ | ○ | ○ | | | | | |
| | AUTONOMIC FUNCTION | SYMPATHETIC, PARASYMPATHETIC | | | | | | | | | | ○ | ○ | ○ | | ○ | | |

FIG. 14

| | | INDEX | | | COMBINATION OF DETERMINATION |
|---|---|---|---|---|---|
| | | OPERATION | HEAD | SIGHTLINE | |
| STRAIGHT | CONSTANT SPEED | -(C1) | ○ | ○ | DETERMINE BY HEAD AND SIGHTLINE |
| | ACCELERATION/DECELERATION | ○ | -(C3) | ○ | DETERMINE BY OPERATION AND SIGHTLINE |
| | FOLLOWING TRAVEL | ○ | ○ | ○ | DETERMINE BY OPERATION, HEAD, SIGHTLINE |
| | AVOIDANCE OF DANGER | ○ | -(C3) | -(C2) | DETERMINE BY OPERATION |
| CURVE | CONSTANT SPEED | ○ | -(C3) | ○ | DETERMINE BY OPERATION AND SIGHTLINE |
| | ACCELERATION/DECELERATION | ○ | -(C3) | ○ | DETERMINE BY OPERATION AND SIGHTLINE |
| | FOLLOWING TRAVEL | ○ | -(C3) | ○ | DETERMINE BY OPERATION AND SIGHTLINE |
| | AVOIDANCE OF DANGER | ○ | -(C3) | -(C2) | DETERMINE BY OPERATION |
| LEFT/RIGHT TURN | | ○ | -(C3) | ○ | DETERMINE BY OPERATION AND SIGHTLINE |
| MERGING | | ○ | ○ | ○ | DETERMINE BY OPERATION AND SIGHTLINE |
| KEEP STOPPING | | -(C1) | ○ | -(C1) | DETERMINE BY HEAD |

STEERING OPERATION IN NORMAL STATE

STEERING OPERATION IN ABNORMAL STATE

FIG. 24

|  |  |  | T11 | | T12 | | T13 | | T13 | |
|---|---|---|---|---|---|---|---|---|---|---|
|  |  |  | CRITERION | DETERMINATION | CRITERION | DETERMINATION | CRITERION | DETERMINATION | CRITERION | DETERMINATION |
| INVOLUNTARY FUNCTION | PERIODICITY CHARACTERISTIC AMOUNT (HEAD BEHAVIOR) |  | LTH | ○ | LTH | ○ | LTH | ○ | LTH | ○ |
|  | SACCADE AMPLITUDE (SIGHTLINE BEHAVIOR) |  | NORMAL AVERAGE RATE LESS THAN 50% | ○ | NORMAL AVERAGE RATE LESS THAN 50% | × | NORMAL AVERAGE RATE LESS THAN 50% | × | NORMAL AVERAGE RATE LESS THAN 50% | × |
|  | ... |  | ... | | ... | | ... | | ... | |
| BASE FUNCTION | STEERING OPERATION DEVIATION DEGREE (DRIVING OPERATION) |  | ESTIMATION ERROR 0.4 deg OR LARGER | ○ | ESTIMATION ERROR 0.4 deg OR LARGER | – | ESTIMATION ERROR 0.35 deg OR LARGER | ○ | ESTIMATION ERROR 0.3 deg OR LARGER | × |
|  | SALIENCY INDEX (SIGHTLINE BEHAVIOR) |  | AREA OVER 0.6: X OR MORE | ○ | AREA OVER 0.6: X OR MORE | – | AREA OVER 0.6: X-α OR MORE | × | AREA OVER 0.6: X-α OR MORE | × |
|  | ... |  | ... | | ... | | ... | | ... | |
| PREDICTIVE FUNCTION | DISTANCE FROM OBSTACLE (DRIVING OPERATION) |  | RISK VALUE Y OR HIGHER | ○ | RISK VALUE Y OR HIGHER | – | RISK VALUE Y OR HIGHER | ○ | RISK VALUE Y-β OR HIGHER | × |
|  | ... |  | ... | | ... | | ... | | ... | |
|  |  |  |  | ○ |  | ○ |  | ○ |  | × |

DRIVER ABNORMALITY DETERMINATION APPARATUS, METHOD AND COMPUTER PROGRAM

CROSS-REFERENCE TO RELATED APPLICATIONS

The present application contains subject matter related to Japanese Priority Application 2020-071671, filed in the Japanese Patent Office on Apr. 13, 2020, the entire contents of which being incorporated herein by reference in its entirety. The application also contains subject matter related to that described in U.S. application Ser. No. 17/198,265, and claiming priority to JP 2020-071670, and in U.S. application Ser. No. 17/198,278, and claiming priority to JP 2020-071673.

TECHNICAL FIELD

A technique disclosed herein relates to a driver abnormality determination apparatus that determines abnormality of a driver who drives a vehicle (hereinafter simply referred to as a driver), for example.

BACKGROUND ART

Recently, development of an automated driving system has been promoted.

The present applicant considers that, at a current moment, the automated driving system is divided largely into two types of automated driving systems.

The first type relates to a system that helps a vehicle to transport an occupant to a destination without a need for an operation by a driver, i.e., fully-automated travel of the vehicle. For example, an automated driving technique is disclosed in Patent document 1. The automated driving technique shifts primary driving responsibility to the vehicle when the occupant performs a specified operation.

The second type relates to an automated driving system that is designed to "provide environment that makes driving of the vehicle enjoyable", that is, with an assumption that a person is responsible for driving. In the automated driving system of the second type, when a situation where the driver is no longer able to drive normally, e.g., suffers from an illness, falls asleep, and the like, the automobile executes automated driving instead of the driver.

Patent document 2 discloses a technique of determining appropriateness of a vehicle driving state by the driver based on a driving posture and an eye-opening amount of the driver that are acquired from an analysis result of a video captured by an imaging section. Patent document 3 discloses a technique of setting a determination criterion for a degree of awareness of the driver and determining an awakening state of the driver based on detected behavior of the driver's head and the set determination criterion. In Non-Patent document 1, a case where the driver had a conscious disturbance attack while driving is discussed.

PRIOR ART DOCUMENTS

Patent Documents

[Patent document 1] JP-A-2019-119373
[Patent document 2] JP-A-2019-79328
[Patent document 3] JP-A-2010-128649

Non-Patent Documents

[Non-Patent document 1] Kazuaki Shinohara and 7 others (November 2014) "Conscious disturbance attack while driving", Transactions of Society of Automotive Engineers of Japan, 45(6), pp. 1105-1110.
[Non-Patent document 2] T. Nakamura, et al., "Multiscale Analysis of Intensive Longitudinal Biomedical Signals and its Clinical Applications", Proceedings of the IEEE, Institute of Electrical and Electronics Engineers, 2016, vol. 104, pp. 242-261
[Non-Patent document 3] Mizuta et al. (2016) "Fractal time series analysis of postural stability", Equilibrium Research, Japan Society For Equilibrium Research, 75(3), pp. 154-161.

SUMMARY

Problems to be Solved

It is important to discover occurrence of abnormality to the driver, in particular, an outbreak of dysfunction or the illness to the driver as soon as possible from perspectives of improving the driver's life-saving rate and ensuring safety of surrounding. In particular, in the second type of automated driving system, the driver has the primary responsible for driving. For this reason, it is extremely important to discover the abnormality of the driver as soon as possible in order to provide an ease of mind and the safety to the driver himself/herself and those around the driver.

A technique disclosed herein has been made in view of such points and therefore has a purpose of simultaneously reducing a time required for a determination of abnormality of a driver and improving accuracy of the determination of the abnormality of the driver.

One or more embodiments are directed to a driver abnormality determination apparatus including circuitry configured to detect a driving operation by a driver and detect a driver state. The circuitry is configured to detect an exertion level of an involuntary function of the driver based on the driver state; detect an exertion level of a driving function of the driver based on the driving operation; and determine driver abnormality on the basis of the exertion level of the involuntary function and the exertion level of the driving function. The circuitry is configured that, on condition that one function level of the exertion level of the involuntary function and the exertion level of the driving function is equal to or lower than a specified determination criterion, relax a determination criterion for the other function level.

Here, the driving operation may be sensed by a sensor for detecting variations in the driving operation by the driver, a decline in driving accuracy, and the like. Examples of the driving operation sensor are an accelerator pedal position sensor, a steering angle sensor, and a brake hydraulic pressure sensor. The driver state sensor is a sensor for detecting biological information such as a driving posture, head behavior, and behavior of eyeballs of the driver. Examples of the driver state sensor are an in-vehicle camera and a biological information sensor. The biological information sensors are a sweat sensor, a heartbeat sensor, a blood flow rate sensor, a temperature sensor that measures a skin temperature, and the like. The driving scenes are a travel scene and a stop scene of the vehicle.

Although a detailed description will be made below, the inventors determined that, from a result of a travel experiment by a sick person using a driving simulator that signs of the driver abnormality, which appear in the detection results by the driving operation sensor and the driver state sensor, appear with a time difference. Thus, it is considered to combine the results acquired by the one or plural sensors of the driver state sensor and the driving operation sensor to improve the accuracy of the driver abnormality determination while accelerating the driver abnormality determination.

However, for example, while the involuntary function, such as of keeping the driver's posture, always must be executed regardless of the driving scene, the driving function (including the predictive driving function and the base function that serves as the basis of the driving operation) is only executed in a situation where the driving operation is performed. Thus, it is difficult to make the determination in a situation other than the above. However, the detection of the involuntary function only is insufficient to determine whether the driver state is a state where the driver is healthy but desultory, a state where fatigue of the driver is accumulated, or a state where the driver suffers from the illness. Accordingly, it is necessary to make the determination under a condition that the abnormal operation matching a specified condition continues for a specified period. That is, the related art has problems that it takes time for the determination when it is attempted to improve the accuracy of the discovery of the illness and that a frequency of an erroneous determination of the illness is increased when it is attempted to reduce the time for the determination of the illness.

For the above reason, in this aspect, the involuntary function detection section and the driving function detection section are provided. The involuntary function detection section detects the execution level of the involuntary function of the driver, and is characterized that the involuntary function detection section can always make measurement regardless of the driving scene but cannot always make the clear determination on the driver. The driving function detection section has an index that can only be used when the driving operation is performed, but is high in detection accuracy of the driver abnormality. Then, by combining the detection results of both detection sections, the driver abnormality is determined early, and the accuracy of the determination of the driver abnormality is improved.

The abnormality determination section may be configured to relax the determination criterion for the execution level of the driving function to facilitate the determination of the driver abnormality in the case where the involuntary function detection section detects that the execution level of the involuntary function is equal to or lower than the specified determination criterion.

The inventors determined that, in the case where the driver suffered from the illness, a function related to high-order action started being declined first, and thereafter, a decline in a function related to base action and a decline in a function related to involuntary action sequentially occurred. However, although a detailed description will be made below, there is a case where the sign of the abnormality of the involuntary function is detected before that of the driving function. Thus, to prepare for such a case, when it is detected that the execution level of the involuntary function is declined to be equal to or lower than the specified determination criterion, the abnormality determination section may lower a determination threshold for the base function level. In this way, the abnormality of the base function level on a curved road or the like thereafter is more likely to be determined. As a result, it is possible to simultaneously discover the driver abnormality early and make the determination with a high degree of accuracy.

The driver abnormality determination apparatus, may be configured that detecting the execution level of the driving function includes detecting: an execution level of a predictive function execution to a predictive driving function of the driver; and an execution level of a base function related to a base function as basis of the driving operation by the driver On condition that the execution level of the predictive function is equal to or lower than a specified determination criterion, the determination criterion for the execution level of the base function may be relaxed.

The inventors determined that, in the case where the driver suffered from an illness, the high-order predictive function started being declined first, and thereafter, a decline in the base function and a decline in the involuntary function sequentially occurred. Accordingly, in the case where the predictive function detection section detects the sign of the abnormality, the driver abnormality can be determined early by reducing a threshold of the determination criterion for the base function level. In particular, embodiments disclosed herein are effective in detection of the driver abnormality in relation to the illness of a cerebral stroke type.

As it has been described so far, according to the technique disclosed herein, it is possible to simultaneously determine the driver abnormality early and improve the accuracy of the abnormality determination.

BRIEF DESCRIPTION OF THE DRAWINGS

FIG. 6A is a table illustrating relationships between measurement indices and driving functions.

FIG. 6B is a table illustrating relationships between measurement indices and the driving functions.

FIG. 14 is a table in which indices that can be evaluated for driving scenes are linked therewith.

FIG. 17 is a view for illustrating a development order of the illness.

FIG. 24 is a table illustrating an example of determination criteria used to determine the driver abnormality and determination results.

DETAILED DESCRIPTION

—Overview—

Merits of a technique of the present disclosure are fully appreciated particularly when such a technique is adopted for the automated driving system in the above-described second directionality, that is, a driver-led automated driving system with an assumption that a person drives a vehicle.

Figure 1:
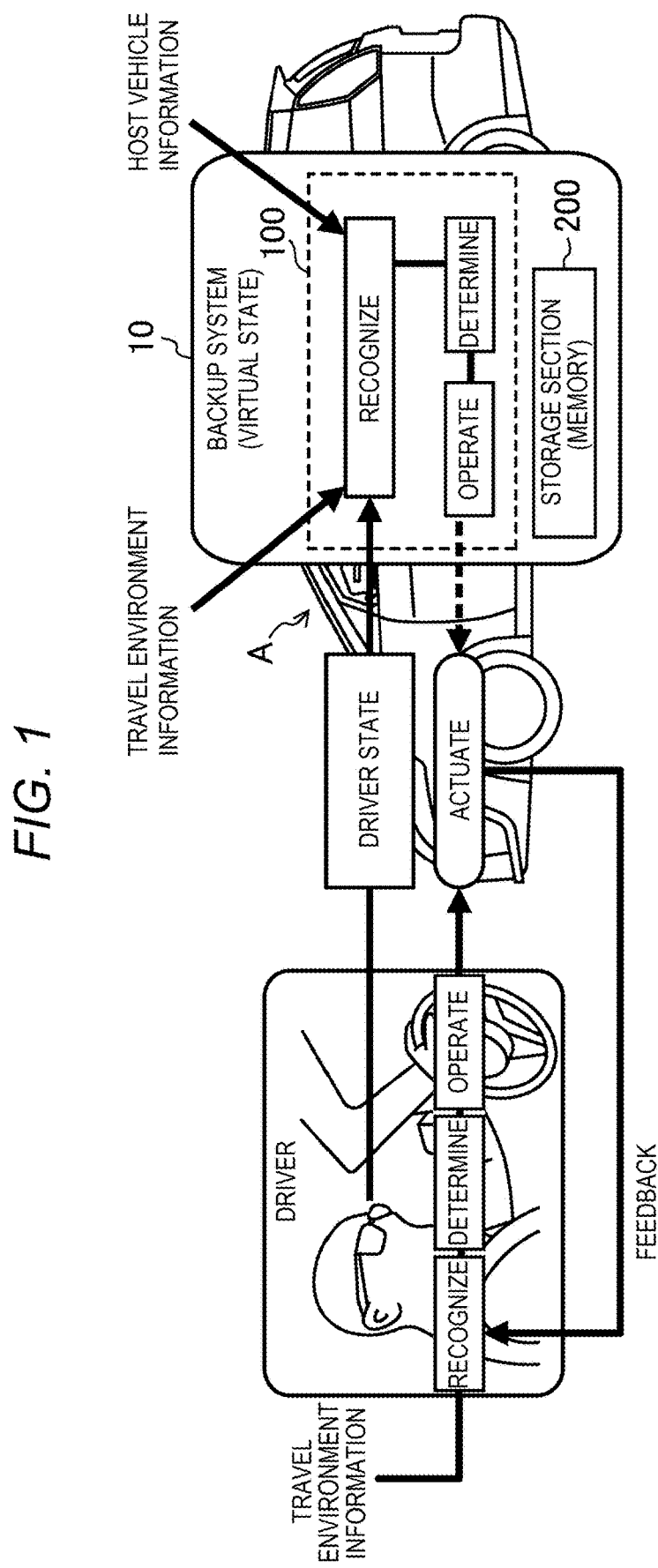
FIG. 1 is a conceptual view for illustrating a driver-led automated driving system.

As illustrated in FIG. 1, regarding a vehicle A on which the driver-led automated driving system is mounted, normally (in a normal state), a driver drives the vehicle A while the automated driving system comprehends states of a host vehicle, external environment, and the driver to perform virtual driving behind the driver. In other words, the automated driving system is operated as a backup system. The automated driving system recognizes travel environment information in a similar manner to the driver, and also recognizes a state of host vehicle information and the driver state. In parallel with driving by the driver, the automated driving system determines how to move the vehicle A based on the recognition results and decides target motion of the vehicle A. When determining that the driver suffers from dysfunction or an illness, the automated driving system operates the host vehicle instead of the driver to ensure safety of surrounding, and also complements a declined function of the driver among functions such as recognition, determination, and the operation.

The driver-led automated driving system is designed with the operation as described above as a precondition. Thus, it is extremely important to discover occurrence of abnormality such as the declined function, the dysfunction, or the illness to the driver (hereinafter referred to as driver abnormality) as soon as possible.

The driver state is largely categorized into a normal healthy state and an abnormal state where the driver suffers from the dysfunction or the illness. The normal state includes, in a descending order of a degree of awareness, a flow state where the driver is concentrated on driving at a maximum, a concentrated driving state, a relaxed driving state, an inattentive driving state, a desultory driving state, a declined awakening state, and a drowsy state. As for the illness, various illnesses exist. Based on the knowledge discussed in Non-Patent document 1, representative examples of the illness that shows a clear sign of a conscious disturbance attack while driving are epilepsy, apoplexy, myocardial infarction, and hypoglycemia.

Figure 2:
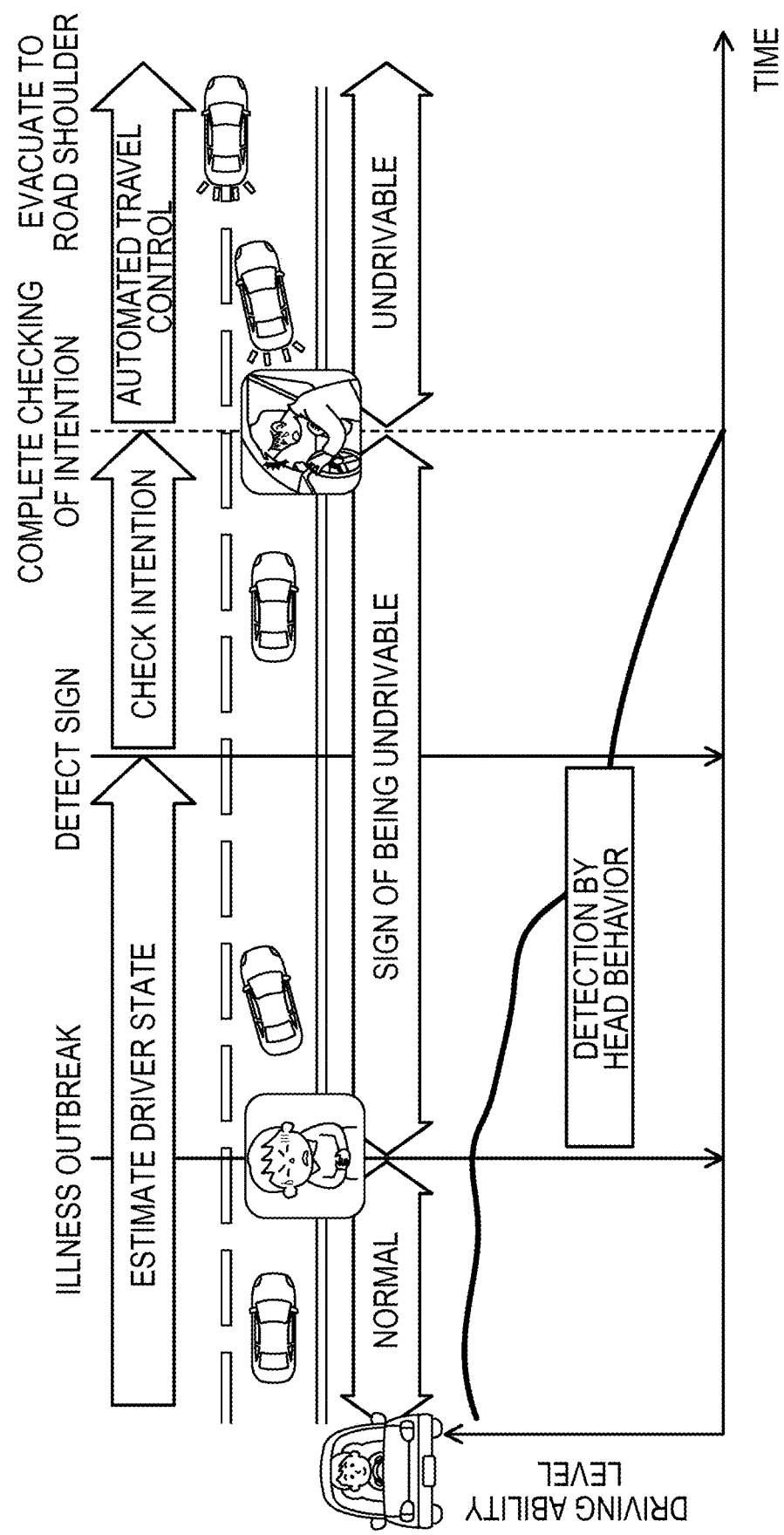
FIG. 2 is a conceptual view illustrating an orientation of a technique that relates to the present disclosure.

The inventors have determined that a state change of the driver from the normal state (the healthy state) to an undrivable state due to the conscious disturbance attack may be categorized into three patterns. A case A is a pattern in which one or some of functions including perception, determination, and mobility are declined first. A case B is a pattern in which the overall functions are gradually declined. A case C is a pattern in which the driver suddenly loses consciousness. Of these, in the cases A, B, as illustrated in FIG. 2, a driving ability level of the driver gradually declines from the outbreak of the illness until the driver eventually reaches an undrivable state. Accordingly, this declined state of the driving ability can be detected.

For all three cases A to C, currently, the outbreak of the illness can be recognized only after the driver is brought into the undrivable state. This is because it is difficult to determine whether the driver is in a state of being healthy but desultory, a state with accumulated fatigue, or a state of suffering from the illness. In addition, in the healthy state of the driver, it is normal that the driver closes eyes and relaxes his/her posture. Thus, the driver abnormality must be determined under a condition that abnormal behavior satisfying a specified condition continues for certain duration. That is, the related art has problems that it takes time to make the determination accurately and that a frequency of an erroneous determination increases when the time required for the determination of the illness is reduced.

[Determination of Driver Abnormality]

<Classification by Driver's Function>

In general, as a method for determining the driver abnormality, that is, a method for determining that the driving ability level is declined and the driver is brought into the undrivable state, a technique of detecting occurrence of abnormality to a function that is established regardless of the driver's intention, a so-called involuntary function has been known. As a method for detecting the abnormality of the involuntary function, for example, there is a method for determining the illness of the driver by analyzing an unbalanced driving posture of the driver and an eye-opening amount of the driver based on a video captured by an imaging section.

Examples of the involuntary function are motor functions of hands and feet, motor functions of a head and eyeballs, an autonomic function such as reaction of an autonomic nerve, and a vestibular function.

When a brain function is focused, in contrast to the involuntary function, a voluntary function that is a voluntary function of a person exists. A voluntary function of the driver that relates to driving will herein be referred to as a "driving function". Recently, various techniques of detecting this driving function have been developed.

The inventors of the present application investigated classification of this driving function by focusing on the brain functions. More specifically, the inventors of the present application classified the driving function into: a base function that is a relatively low-order function (hereinafter also referred to as a low-order function); and a predictive driving function (hereinafter simply referred to as a predictive function) that is a relatively high-order function (hereinafter referred to as a high-order function).

The base function is a driving function that serves as a base (basis or a foundation) of a driving operation, and is a driving function that is processed in a barely conscious region. Examples of the base function are a perceptual function of a position and motion, a range of vision, the motor functions of the arms and the legs, the motor functions of the head and the eyeballs, and a function related to spatial recognition. More specifically, examples of the base function are a driving function of making the vehicle travel along a lane, a driving function of making the vehicle travel while keeping an inter-vehicular distance with a preceding vehicle, and a driving function of making the vehicle stop in front of a red light or a crosswalk.

The predictive function is a function of predicting a future driving scene, and is a driving function that impacts on whether so-called "forecasting possible occurrence of something" can be performed. Examples of the predictive function are a risk predictive function of predicting a risk during driving, a determination function related to the driving action, and an attention function during driving. The risk predictive function includes a function of predicting a potential risk, a function of predicting approach of a visible risk, a function of predicting a risk that is based on travel environment such as a road shape, and the like. The attention function during driving includes a function of concentrating on a matter to be concentrated, a function of appropriately allocating the attention, a spatial attention function, and the like.

Figure 3:
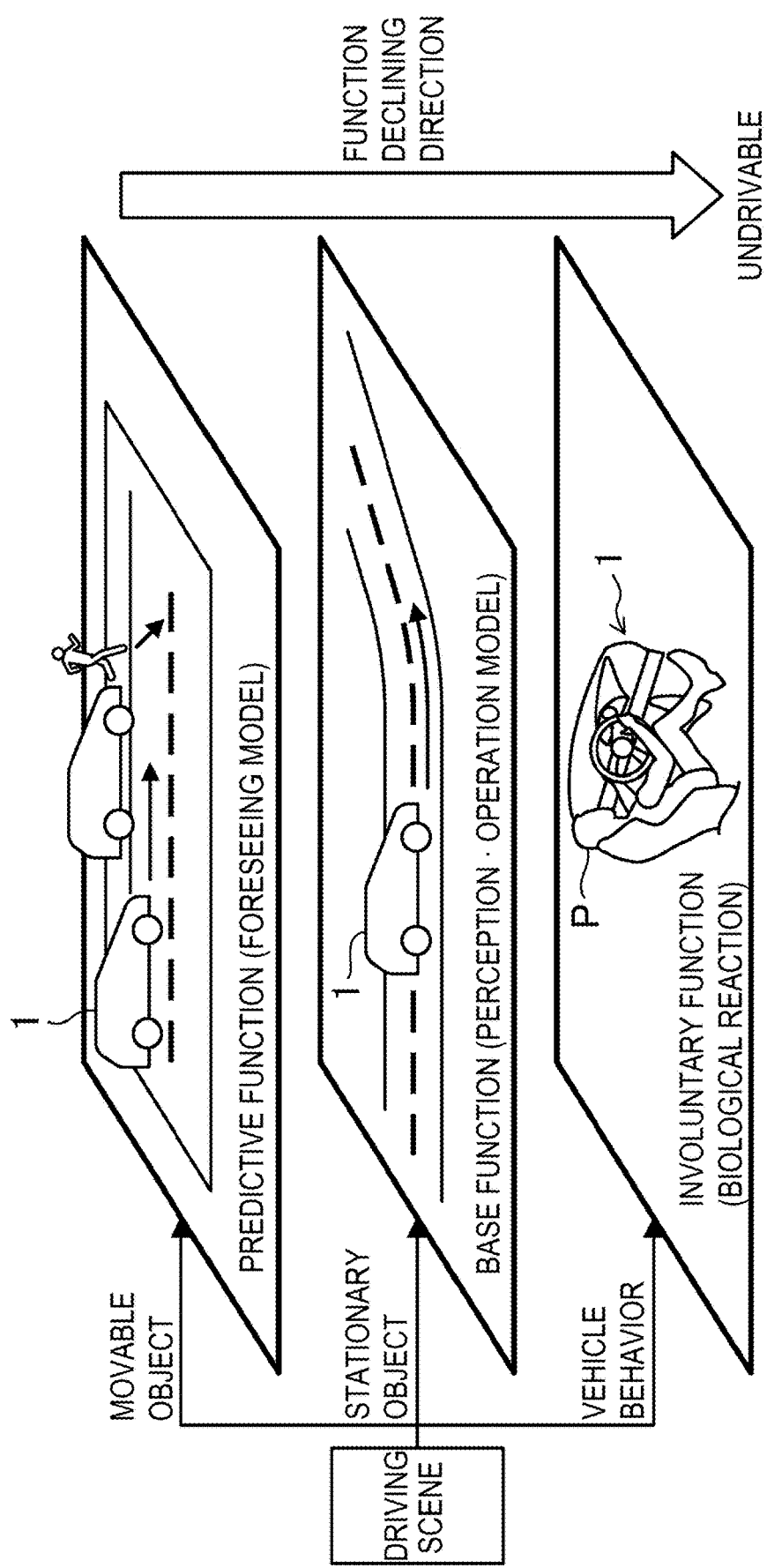
FIG. 3 is a view for illustrating stratification of driving action of a driver.

In summary, as illustrated in FIG. 3, the inventors investigated to divide the driving action of the driver into three strata of involuntary action with which the above-described involuntary function was executed, base action with which the base function was executed, and predictive action where the predictive function was executed. Then, the inventors investigated to determine the driver abnormality by using an involuntary function level indicative of a degree of proper execution of the involuntary function, a base function level indicative of a degree of proper execution of the base function, and a predictive function level indicative of a degree of proper execution of the predictive function. As a specific method, the inventors conducted travel tests on a healthy person and a sick person by using a driving simulator to change the driving scene and a driving situation. Then, the inventors analyzed the results. As a result, the inventors obtained knowledge that, in the case where the driver suffered from the illness, the function related to the high-order action started being declined first, and thereafter, the decline in the function related to the base action and then the decline in the function related to the involuntary action sequentially occurred.

Furthermore, to improve accuracy of the determination of the driver abnormality, the involuntary function level, the base function level, and/or the predictive function level may be combined to determine the driver abnormality. As a result, the inventors determined that, in the case where the functions as the basis of the driving ability were classified into the involuntary function, the low-order function, and the high-order function, there were a case where each of such functions was suited for the detection of the driver abnormality and a case where each of such functions was not suited for the detection of the driver abnormality according to the driving scene of the vehicle (including a traffic condition). That is, the driver abnormality may be determined early and the accuracy thereof may be improved by paying attention to a relationship between the vehicle driving scene and suited timing for detection of the abnormality of each of the above functions when the involuntary function level, the base function level, and/or the predictive function level were combined.

<Combination of Detection of Functions>

Figure 4:
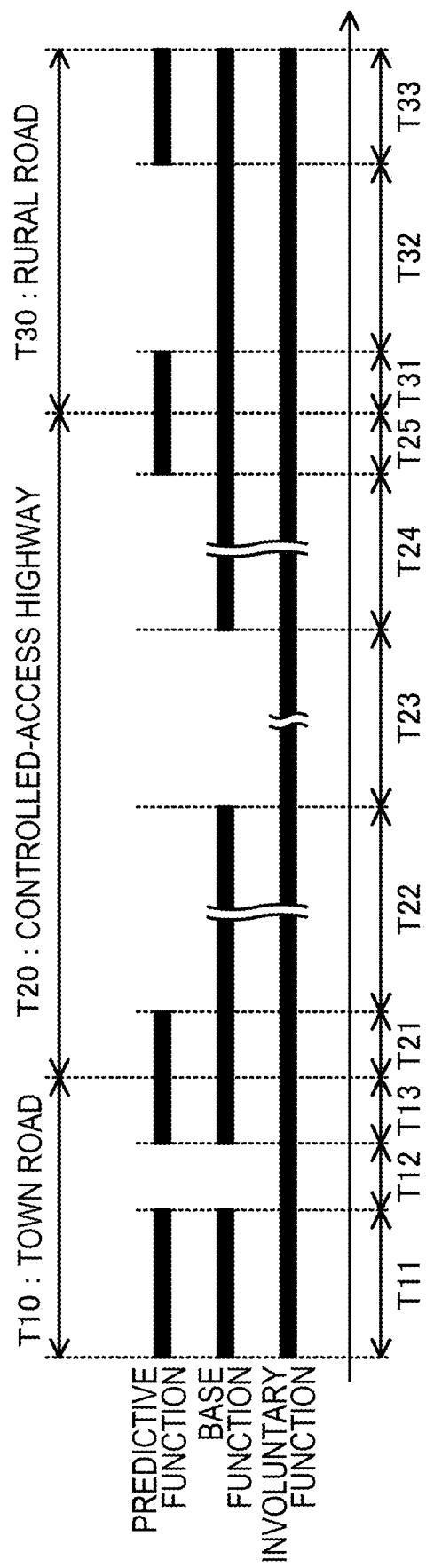
FIG. 4 is a chart illustrating timing at which each function of the driver during driving can be determined.

FIG. 4 is a chart illustrating an example of suited timing for the determination of each of the functions, which are the predictive function, the base function, and the involuntary function, per driving scene.

In FIG. 4, in the driving scene in a period T10 (including T11 to T13), the vehicle A (the host vehicle) travels on a town road on which a pedestrian, a parked vehicle, and the like exist. It is assumed that the vehicle travels on the town road at a specified speed in the periods T11, T13 and that the vehicle stops at a signal, a crosswalk, or the like in the period T12. In the present disclosure, the term "driving scene" is used as a concept that includes, in addition to the travel scene of the vehicle, a scene where the vehicle stops for a specified time at a stop sign, the signal, or the like.

Since the vehicle A travels on the town road in the periods T11, T13, the vehicle A is in a situation where the predictive function must be executed to avoid the parked vehicle, to predict running of the pedestrian into the road, and the like. The vehicle A is also in a situation where the base function must be executed to keep the constant inter-vehicular distance with the preceding vehicle, to travel along the lane at a curve, and the like. Furthermore, the involuntary function must be executed to keep looking forward, keep a driving posture, and the like. That is, in the periods T11, T13, the vehicle A is in a situation where the involuntary function, the base function, and the predictive function all must be executed, and such a situation corresponds to a driving scene suited to detect the driver abnormality or the sign of the driver abnormality (hereinafter collectively and simply referred to as the "driver abnormality") related to the involuntary function, the base function, and the predictive function. Accordingly, in a driving scene as that in the periods T11, T13, an abnormality determination apparatus determines the driver abnormality by checking results of the function levels of the driver and a combination thereof with a specified condition or standard. The function levels of the driver are detected by (1) an involuntary function detection section that detects the involuntary function level, (2) a predictive function detection section that detects the predictive function level, and (3) a base function detection section that detects the base function level. The involuntary function detection section, the predictive function detection section, and the base function detection section will be described below in an embodiment.

In the period T12, the vehicle A stops. Thus, there are many situations where the base function and/or the predictive function does not have to be executed while the involuntary function still must be executed. In such a case, significant data may not be acquired even when execution statuses of the base function and the predictive function with respect to the driver's action are detected, and the insignificant data thereon possibly becomes noise in estimation of the driver abnormality. Thus, in the driving scene as that in the period T12, the abnormality determination apparatus determines the driver abnormality based on the detection result by the involuntary function detection section.

In a driving scene in a period T20 (including T21 to T25), the vehicle A (the host vehicle) travels on a limited highway with no signals such as a controlled-access highway or a toll road (described as "CONTROLLED-ACCESS HIGHWAY" in FIG. 4). For example, it is assumed that the period T21 represents a period from time at which the vehicle A arrives at a toll booth to time at which the vehicle A merges into a travel lane, the periods T22 to 124 represent periods in each of which the vehicle A travels on the travel lane, and the period T25 represents a period from time at which the vehicle A enters a frontage road from the travel lane to time at which the vehicle A leaves the toll booth. In addition, it is assumed that the period T23 corresponds to such a driving scene that no vehicle is present around the host vehicle and the host vehicle travels on a long straight road. That is, it is assumed that the period T23 corresponds to a situation where the driver hardly needs to be aware of a surrounding situation and only needs to drive the vehicle in a straight line.

The periods T21, T25 each correspond to a situation where the predictive function must be executed in order to predict a risk of the approach of the vehicle from the right or the left at the toll booth, to predict a risk related to behavior of another vehicle during merging, and the like. In addition, the periods T21, T25 each correspond to a situation where the base function must be executed in order to keep the constant inter-vehicular distance with the preceding vehicle and to travel along the lane at the curve. Furthermore, the periods T21, T25 each correspond to a situation where the involuntary function must be executed to keep looking forward, keep the driving posture, and the like. That is, the periods T21, T25 each correspond to a situation where the involuntary function, the base function, and the predictive function must be executed and to a driving scene suited to detect the abnormality of the involuntary function, the base function, and the predictive function. Accordingly, in a driving scene as that in the periods T21, T25, similar to the case in T11, the abnormality determination apparatus determines the driver abnormality by checking the results of the function levels of the driver, which are detected by the involuntary function detection section, the predictive function detection section, and the base function detection section, and the combination thereof with the specified condition or standard.

The periods T22, T24 each correspond to a situation where the base function must be executed to keep the constant inter-vehicular distance with the preceding vehicle, to travel along the lane at the curve, and the like. Furthermore, the periods T22, T24 each correspond to the situation where the involuntary function must be executed to keep looking forward, keep the driving posture, and the like. Meanwhile, such a situation possibly arises where the predictive functions including the risk predictive function and the attention function do not have to be executed when a distance from another peripheral vehicle is long or when the vehicle A travels solo. In such a driving scene, significant data may not be acquired even when the execution status of the predictive function of the driver is detected, and the insignificant data thereon possibly becomes the noise in the estimation of the driver abnormality. Accordingly, in a driving scene as that in the periods T22, T24, such a situation arises that at least the involuntary function and the base function must be executed. Thus, the abnormality determination apparatus determines that the involuntary function and the base function are suited to detect the abnormality, and determines the driver abnormality by checking the results of the function levels of the driver, which are detected by the involuntary function detection section and the base function detection section, and the combination thereof with the specified condition or standard.

The period T23 corresponds to a situation where the base function must be executed in order for the vehicle A to travel along the lane. However, even in a situation where the base function is not sufficiently executed, such a situation is less likely to impact on the travel of the vehicle A. In other words, in a driving scene such as that in the period T23, the driver does not have to execute the base function sufficiently. Accordingly, in such a driving scene, the significant data may not be acquired even when the execution status of the base function with respect to the driver's action is detected, and the insignificant data thereon possibly becomes the noise in the estimation of the driver abnormality. The same applies to the predictive function. Accordingly, in the driving scene as that in the period T23, such a situation arises that at least the involuntary function must be executed. Thus, the abnormality determination apparatus determines that the involuntary function is suited to detect the abnormality, and determines the driver abnormality based on the detection result by the involuntary function detection section.

In a driving scene in a period T30 (including T31 to T33), the vehicle A (the host vehicle) travels on a rural road. In particular, in the period T32, it is assumed that the pedestrian, a bicycle, and the like are not present and that the vehicle A travels on a road in a relatively monotonous shape at a specified speed.

The periods T31, T33 each correspond to a situation where the predictive function must be executed to avoid the parked vehicle, to predict running of the pedestrian into the road, and the like. Accordingly, similar to the case in the above-described period T11, the abnormality determination apparatus determines the driver abnormality by checking the results of the function levels of the driver, which are detected by the involuntary function detection section, the predictive function detection section, and the base function detection section, and the combination thereof with the specified condition or standard.

Here, the detection of whether the driving function (the high-order and low-order voluntary functions) or the involuntary function is executed means detection made for purposes of life saving and ensuring safety by the early determination of the driver abnormality, and includes aspects such as the estimation and the determination in apparatus hardware. In addition, the detection by the apparatus of embodiments is a different concept from a determination that is made by a medical practitioner who sees a human body and determines whether the human body functions normally.

A further specific description will be made on a configuration example and an operation example of the abnormality detection apparatus in the following embodiment.

Embodiment (Vehicle Controller)

Figure 5:
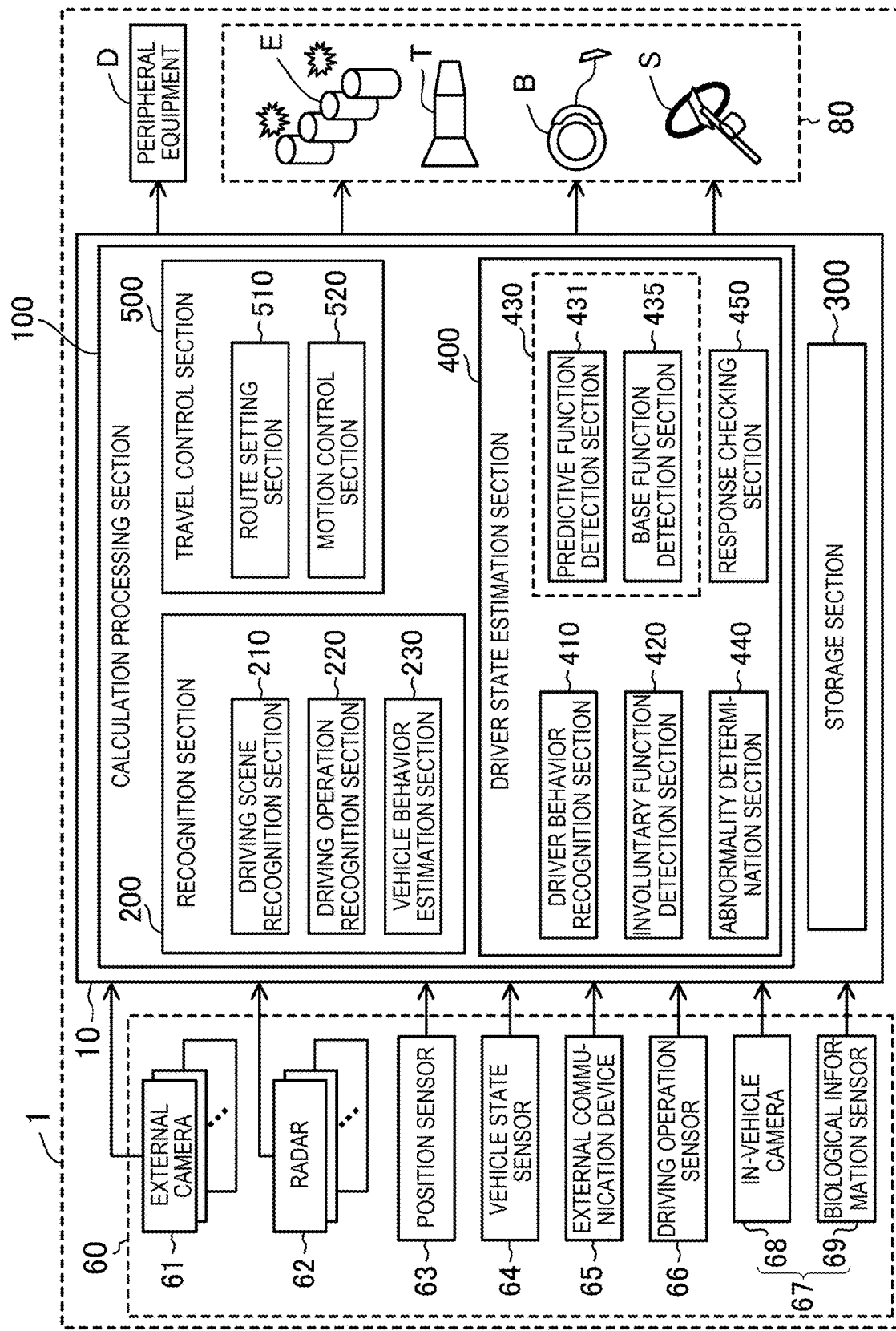
FIG. 5 is a block diagram illustrating a functional configuration of an automotive operating device.

FIG. 5 exemplifies a configuration of a vehicle controller 10 according to the embodiment. A vehicle control system 1 is provided in a vehicle. The vehicle A can be switched among manual driving, assisted driving, and automated driving. The manual driving is driving in which the vehicle A travels according to an operation by the driver (for example, an operation of an accelerator pedal or the like). The assisted driving is driving in which the vehicle A travels while the operation by the driver is assisted. The automated driving is driving in which the vehicle A travels without the operation by the driver. The vehicle controller 10 controls the vehicle A in the assisted driving and the automated driving. More specifically, the vehicle controller 10 controls operation (particularly, the travel) of the vehicle A by controlling an actuator 80 that is provided in the vehicle A.

[Information Acquisition Apparatus]

An information acquisition apparatus 60 at least acquires information for specifying the driving scene of the vehicle A and information for specifying the driver state. The driving scenes of the vehicle A include the travel scene and the stop scene of the vehicle. The information acquisition apparatus 60 includes plural external cameras 61, plural radars 62, a position sensor 63, a vehicle state sensor 64, an external communication device 65, a driving operation sensor 66, and a driver state sensor 67.

<External Camera>

The plural external cameras 61 are provided in a manner capable of capturing images of environment around the vehicle A (including an on-road obstacle, hereinafter referred to as external environment), and capture images of the external environment, for example. Imaging data that is acquired by each of the plural external cameras 61 is transmitted to the vehicle controller 10. The external camera 61 is an example of an external environment acquisition device that acquires external environment information of the vehicle A (hereinafter simply referred to as the external environment acquisition device). The imaging data of the external camera 61 is an example of the external environment information for specifying the driving scene of the vehicle A (hereinafter simply referred to as the external environment information). The external camera 61 means a general camera that captures the image of the exterior environment, and includes a camera that is provided in a cabin and captures an image of the outside of the vehicle.

Each of the plural external cameras 61 is a monocular camera having a wide-angle lens. For example, the external camera 61 is configured by using solid-state imaging elements such as a charge-coupled device (CCD) and a complementary metal-oxide-semiconductor (CMOS). Here, the external camera 61 may be a monocular camera having a narrow-angle lens or a stereo camera having a wide-angle lens or a narrow-angle lens.

The external cameras 61 may include an image sensor that takes fixed and/or moving images in the visual spectrum and/or non-visual ranges such as infrared and ultraviolet.

<Radar>

The plural radars 62 are attached to a body or the like of the vehicle A in a manner capable of detecting an object (including the on-road obstacle) in the external environment, that is, capable of emitting a radio wave, which is used to detect the object, toward the outside of the vehicle. Image data that is acquired by each of the plural radars 62 is transmitted to the vehicle controller 10.

Although a type of the radar 62 is not particularly limited, examples of the radar 62 are a millimeter-wave radar using a millimeter wave, a lidar (light detection and ranging) using a laser beam, an infrared radar using infrared light, and an ultrasonic radar using an ultrasonic wave. A detection result by the radar 62 is an example of the external environment information.

<Position Sensor>

The position sensor 63 detects a position (for example, a latitude and a longitude) of the vehicle. For example, the position sensor 63 receives GPS information from the Global Positioning System and detects the position of the vehicle based on the GPS information. The information (the position of the vehicle) that is acquired by the position sensor 63 is transmitted to the vehicle controller 10. The positional information of the vehicle that is detected by the position sensor 63 can be used to specify the driving scene of the vehicle. That is, the position sensor 63 is an example of an external information acquisition device, and the positional information of the vehicle A, which is detected by the position sensor 63, is an example of the external environment information.

<Vehicle State Sensor>

The vehicle state sensor 64 detects a state (for example, a speed, acceleration, a yaw rate, or the like) of the vehicle. Examples of the vehicle state sensor 64 are a vehicle speed sensor that detects the speed of the vehicle, an acceleration sensor that detects the acceleration of the vehicle, and a yaw rate sensor that detects the yaw rate of the vehicle. Information (the vehicle state) that is acquired by the vehicle state sensor 64 is transmitted to the vehicle controller 10.

<External Communication Device>

The external communication device 65 receives various types of information through an external network (for example, the Internet or the like) that is provided on the outside of the vehicle. For example, the external communication device 65 receives information on another vehicle from the other vehicle located around the vehicle, and receives car navigation data, traffic information, high-precision map information, and the like from a navigation system. The information that is acquired by the external communication device 65 is transmitted to the vehicle controller 10. The information such as the traffic information and the high-precision map information that is acquired by the external communication device 65 from the external network includes information for specifying the driving scene of the vehicle A. That is, the external communication device 65 is an example of the external information acquisition device, and the information received by the external communication device 65 is an example of the external environment information.

<Driving Operation Sensor>

The driving operation sensor 66 detects the driving operation on the vehicle. Examples of the driving operation sensor 66 are an accelerator pedal position sensor, a steering angle sensor, and a brake hydraulic pressure sensor.

The accelerator pedal position sensor detects an operation amount of an accelerator pedal of the vehicle A. The steering angle sensor detects a steering angle of a steering wheel of the vehicle A. The brake hydraulic pressure sensor detects an operation amount of a brake of the vehicle A. The information (the driving operation of the vehicle) that is acquired by the driving operation sensor 66 is transmitted to the vehicle controller 10. The driving operation sensor 66 can detect the driver state from the driving operation. That is, the driving operation sensor 66 can also be used as the driver state sensor.

<Driver State Sensor>

The driver state sensor 67 detects the state of the driver who drives the vehicle (for example, body behavior, biological information, and the like of the driver). Information (the driver state) that is acquired by the driver state sensor 67 is transmitted to the vehicle controller 10. Examples of the driver state sensor 67 are an in-vehicle camera 68 and a biological information sensor 69.

In-Vehicle Camera

For example, the in-vehicle camera 68 is installed in front of the driver such that the driver's eyeballs are positioned within an imaging area. The in-vehicle camera 68 acquires image data including the driver's eyeballs by capturing an image of an area including the driver's eyeballs. Imaging data by the in-vehicle camera 68 is transmitted to the vehicle controller 10. The in-vehicle camera 68 may be provided on goggles worn by the driver.

Biological Information Sensor

The biological information sensor 69 detects the biological information (for example, sweating, heartbeats, a blood flow rate, a skin temperature, and the like) of the driver. The information (the biological information of the driver) that is acquired by the biological information sensor 69 is transmitted to the vehicle controller 10.

[Vehicle Controller]

The vehicle controller 10 includes a calculation processing section 100 and a storage section 300. The calculation processing section 100 has a driving scene recognition section 210, a driving operation recognition section 220, a vehicle behavior estimation section 230, a travel control section 500, and a driver state estimation section 400.

The vehicle controller 10 includes a processor (corresponding to the calculation processing section 100) and memory (corresponding to the storage section 300), for example. The memory stores a module as software that can be run by the processor. A function of each of the sections in the vehicle controller 10 illustrated in FIG. 5 is executed, for example, when the processor executes respective one of the modules stored in the memory. The memory also stores data on a model that is used by the vehicle controller 10.

The plural processors and plural pieces of the memory may be provided. In addition, the functions of the sections in the calculation processing section 100 illustrated in FIG. 5 may be executed by a hardware circuit. The calculation processing section 100 will be described below. Optionally, the calculation processing section 100 may include a processor 835 and other circuitry in system 800 of FIG. 25, which may be implemented as a single processor-based system, or a distributed processor-based system, including remote processing, such as cloud-based processing.

<Recognition Section>

A recognition section 200 includes the driving scene recognition section 210, the driving operation recognition section 220, and the vehicle behavior estimation section 230.

<Driving Scene Recognition Section>

The driving scene recognition section 210 recognizes the driving scene of the vehicle based on the external environment information that is acquired by the external information acquisition device. More specifically, the driving scene recognition section 210 recognizes the driving scene of the vehicle by using the external environment information that is acquired by one or plural of the external cameras 61, the radars 62, the position sensor 63, the external communication device 65, and the vehicle behavior estimation section 230.

For example, the driving scene recognition section 210 provides a learning model, which is generated by deep learning, with the external environment information as input, to generate driving scene information on the driving scene of the vehicle. In the deep learning, a deep neural network is used. An example of the deep neural network is a convolutional neural network (CNN).

For example, the driving scene recognition section 210 performs image processing on the image that is captured by the external camera 61, and thereby generates two-dimensional map data on an area where the vehicle A can move. In addition, the driving scene recognition section 210 acquires object information that is information on an object existing around the vehicle A based on the detection results by the radars 62. Based on the object information, the driving scene recognition section 210 recognizes the on-road obstacle among the objects existing around the vehicle A, and the on-road obstacle can be an obstacle in a process of traveling and stopping of the vehicle A. Examples of the object are a movable object that is displaced over time and a stationary object that is not displaced over time. Examples of the movable object are a four-wheeled motor vehicle, a two-wheeled motor vehicle, the bicycle, and the pedestrian. Examples of the stationary object are a traffic sign, a roadside tree, a median strip, a center pole, and a building. The object information includes positional coordinates of the object, a speed of the object, and the like. Here, the driving scene recognition section 210 may acquire the object information based on the images acquired by the external cameras 61 in addition to or instead of the detection results by the radars 62. Then, the driving scene recognition section 210 integrates the two-dimensional map data and the object information to generate integrated map data (three-dimensional map data) on the external environment, and updates the map data at specified time intervals to recognize the driving scene of the vehicle.

<Driving Operation Recognition Section>

The driving operation recognition section 220 recognizes the driving operation on the vehicle by the driver based on output of the driving operation sensor 66. More specifically, for example, the driving operation recognition section 220 detects operations of the accelerator pedal, the brake pedal, the steering wheel, a shift lever, a direction indicator, and an electrical component by the driver, for example. The driving operation recognition section 220 may improve recognition accuracy of the driving operation by referring to the driving scene information by the driving scene recognition section 210 in addition to the input of the driving operation sensor 66.

<Vehicle Behavior Estimation Section>

The vehicle behavior estimation section 230 estimates behavior (for example, the speed, the acceleration, the yaw rate, and the like) of the vehicle based on the output of the vehicle state sensor 64. For example, the vehicle behavior estimation section 230 generates vehicle behavior data on the behavior of the vehicle based on the output of the vehicle state sensor 64 by using the learning model that is generated by the deep learning.

For example, the learning model that is used by the vehicle behavior estimation section 230 is a vehicle six-axis model. In the vehicle six-axis model, the acceleration in three axial directions of "front/rear", "right/left", and "up/down" and angular velocities in three axial directions of "pitch", "roll", and "yaw" of the traveling vehicle are modeled. That is, the vehicle six-axis model is a numerical model that replicates the behavior of the vehicle by using a total of six axes including pitching (a Y-axis) and rolling (an X-axis) motion and movement in a Z-axis (vertical motion of a vehicle body) of the vehicle body placed on four wheels via suspensions instead of capturing motion of the vehicle only on a traditional vehicle dynamics plane (only front/rear and right/left (X-Y movement) and yaw motion (the Z-axis) of the vehicle).

<Travel Control Section>

The travel control section 500 includes a route setting section 510 and a motion control section 520.

Route Setting Section

The route setting section 510 generates one or plural candidate routes, on each of which the vehicle travels to a target position as a travel target of the vehicle, based on the driving scene recognized by the driving scene recognition section 210. For example, of the plural candidate routes, the route setting section 510 selects the route that the driver feels the most comfortable, and outputs such a route as a travel target route of the vehicle A to the motion control section 520. In addition, for example, in case of such emergency that the driver state estimation section 400 detects the driver abnormality, the route setting section 510 searches for a stop position at which the vehicle stops emergently, sets the stop position as the target position, and generates an evacuation route to the stop position. Then, the route setting section 510 outputs the evacuation route as the travel target route to the motion control section 520.

Motion Control Section

The motion control section 520 determines target motion that is motion of the vehicle required for travel on the travel target route set by the route setting section 510, and controls the actuator 80 based on the determined target motion. For example, the motion control section 520 derives target drive power, a target braking force, and a target steering amount that are required to produce the target motion. Then, the motion control section 520 transmits a drive command value indicative of the target drive power, a brake command value indicative of the target braking force, and a steering command value indicative of the target steering amount to the actuator for a drive system, the actuator for a brake system, and the actuator for a steering system, respectively. Examples of the actuator for the drive system are an engine E, a transmission T, and a motor. An example of the actuator for the brake system is a brake B. An example of the actuator for the steering system is a steering wheel S. In the present disclosure, the term actuator 80 is used as a collective term of the actuator for the drive system, the actuator for the brake system, and the actuator for the steering system. In addition, equipment other than the actuators 80 that is mounted to the vehicle A will collectively be referred to as peripheral equipment D. Examples of the peripheral equipment D are an information display D1 such as a monitor in a car navigation system, a speaker D2 for playing voices and the like, various switches D3 including an engine start switch and driver response switch, a microphone D4 for inputting the driver's voice, and lighting devices such as a headlamp and the direction indicator.

<Driver State Estimation Section>

The driver state estimation section 400 includes a driver behavior recognition section 410, an involuntary function detection section 420, a driving function detection section 430, a response checking section 450, and an abnormality determination section 440. The driver state estimation section 400 has a function of detecting an abnormal physical condition of the driver. Thus, the vehicle controller 10 including the driver state estimation section 400 is an example of the driver abnormality determination apparatus that determines the abnormal physical condition of the driver.

Driver Behavior Recognition Section

The driver behavior recognition section 410 detects the behavior of the driver (including behavior of the head and behavior of a sightline) based on the output of the driver state sensor 67. For example, the driver behavior recognition section 410 includes: a head behavior detection section 411 (see FIG. 7) that detects the behavior of the driver's head based on the imaging data by the in-vehicle camera 68; and a sightline behavior detection section 412 (see FIG. 11) that detects behavior of the driver's sightline on the basis of the imaging data by the in-vehicle camera 68. The head behavior detection section 411 and the sightline behavior detection section 412 will be described below.

Involuntary Function Detection Section

The involuntary function detection section 420 detects the driver abnormality that is based on the involuntary function based on the detection data by the driver state sensor 67 that detects the driver state. More specifically, as described above, the detection data by the driver state sensor 67 is transmitted to the driver behavior recognition section 410. Then, the involuntary function detection section 420 detects the driver abnormality that is based on the involuntary function based on the output of the driver behavior recognition section 410. For example, the involuntary function detection section 420 calculates the involuntary function level of such a degree that the involuntary function of the driver is executed normally. The driver state sensor herein includes the driving operation sensor 66 in addition to the driver state sensor 67. That is, there is a case where the driver state can be detected by using the driving operation sensor 66. In such a case, the driving operation sensor 66 is included in the driver state sensor in the technique of the present disclosure. The same applies to the other components of the information acquisition apparatus 60. The involuntary function detection section 420 may have the function of the driver behavior recognition section 410, and the detection data by the driver state sensor 67 may directly be input to the involuntary function detection section 420 for processing.

For example, as the involuntary function levels regarding the driving operation by the driver, the involuntary function detection section 420 (1) can detect a motor function level of the right foot on the basis of the detection data by the accelerator pedal position sensor, (2) can detect a motor function level of the left foot on the basis of the detection data by the brake hydraulic pressure sensor, and (3) can detect a motor function level of the right hand and/or the left hand on the basis of the detection data by the steering angle sensor (see a lower portion of FIG. 6A). Here, the motor function level is an index that indicates a degree that the motor function is executed normally. FIG. 6A and FIG. 6B are tables, each of which illustrates relationships between detection target items and the function levels that can be measured for the items. For example, the storage section 300 stores the tables in FIG. 6A and FIG. 6B and a determination condition for determining the driver abnormality, which is described below in a corresponding manner.

For example, as the involuntary function levels regarding the behavior of the driver's sightline, based on the behavior of the driver's sightline recognized by the sightline behavior detection section 412, the involuntary function detection section 420 (1) can detect the motor function level of a pupillary reflex by calculating microsaccades, (2) can detect the motor function level of the pupillary reflex by calculating an amount of nystagmus, and (3) can detect an autonomic function level of a sympathetic nerve/a parasympathetic nerve of the driver by calculating turn of the eyeballs. In addition, the involuntary function detection section 420 can detect a vestibular function level of a vestibular reflex by calculating temporal changes in pupil diameters of the driver based on the imaging data of the sightline by the in-vehicle camera 68 (see the lower portion in FIG. 6B). Here, the vestibular function level is an index that indicates a degree that the vestibular function is executed normally. Here, the autonomic function level is an index that indicates a degree that the autonomic function is executed normally.

For example, as the involuntary function levels regarding the behavior of the driver's head, the involuntary function detection section 420 (1) can detect the autonomic function level of the sympathetic nerve/the parasympathetic nerve of the driver by calculating autocorrelation of the head behavior, (2) can detect the vestibular function level of a vestibulo-ocular reflex of the driver by calculating cross-correlation between the head and the sightline on the basis of the behavior of the driver's head and the behavior of the driver's sightline, and (3) can detect the autonomic function level of the sympathetic nerve/the parasympathetic nerve of the driver by calculating cross-correlation between the head behavior and an external force on the basis of the behavior of the driver's head and the estimation result of an external force to the driver by the vehicle state sensor 64 (see a lower portion of FIG. 6B).

Driving Function Detection Section

The driving function detection section 430 detects a driving function level of such a degree that the driving function of the driver is executed normally based on detection data by a driving motion sensor that detects motion of the driver during driving (hereinafter referred to as driving motion). The driving motion sensors herein are the driving operation sensor 66 and the driver state sensor 67. More specifically, the driving function detection section 430 detects the driving function of the driver based on a situation of the driving operation by the driver, which is detected by the driving operation sensor 66, and the driver state, which is detected by the driver state sensor 67 (for example, the in-vehicle camera 68 and the like). As described above, the detection data by the driving motion sensor is partially or entirely transmitted to the driver behavior recognition section 410, which in turn recognizes the driver state. Accordingly, the driving function detection section 430 may use a recognition result of the driver behavior recognition section 410 (for example, the head behavior detection section 411 and/or the sightline behavior detection section 412).

The driving function detection section 430 includes: a predictive function detection section 431 that detects the above-described predictive function level; and a base function detection section 435 that detects the above-described base function level.

Predictive Function Detection Section

The predictive function detection section 431 detects the predictive function level based on the driving operation by the driver, the behavior of the driver's sightline, and/or the behavior of the driver's head, for example.

For example, the predictive function level that is based on the driving operation by the driver can be detected by a calculation using the driving scene recognized by the driving scene recognition section 210 and a steer model (hereinafter also referred to as a steer model calculation). More specifically, for example, a spatial attention function level can be detected per driving scene based on a feedback (FB) gain of steering and/or an estimation error between a model operation and an actual operation of the steering wheel (see an upper portion of FIG. 6A). Here, in the steer model, steering and a support structure of steering are modeled. When steering force data that is associated with a steering operation by the driver is input, data on a transition force in a lateral direction of the vehicle is output based on this steering force data.

In addition, for example, the predictive function level that is based on the driving operation by the driver can be detected by a calculation using the driving scene recognized by the driving scene recognition section 210 and a risk prediction model (hereinafter also referred to as a risk model calculation). More specifically, for example, per driving scene, (1) the risk predictive function level with respect to the potential risk and attention function levels related to concentration and allocation can be detected on the basis of a magnitude of the potential risk calculated by the risk model calculation, (2) the risk predictive function level with respect to the visible risk, the attention function level related to the concentration and the allocation, and the spatial attention function level can be detected on the basis of a magnitude of the visible risk calculated by the risk model calculation, and (3) the risk predictive function levels with respect to the potential risk, the visible risk, and the road shape, the attention function levels related to the concentration and the allocation, and the spatial attention function level can be detected on the basis of deviation from a low-risk state calculated by the risk model calculation (see the upper portion of FIG. 6A). Here, a type and a content of the risk prediction model are not particularly limited. For example, in the risk prediction model, a risk potential of the host vehicle and a risk potential of the preceding vehicle are set based on a relative speed and a relative distance between the host vehicle and the preceding vehicle, and a risk that can be predicted from these risk potentials is modeled. Here, the risk predictive function level is an index that indicates a degree that the risk predictive function is executed normally. In addition, the attention function level is an index that indicates a degree that the attention function is executed normally.

In addition, for example, the predictive function level that is based on the driving operation by the driver can be detected by a calculation using the driving scene recognized by the driving scene recognition section 210 and a road shape prediction model (hereinafter also referred to as a road model calculation). More specifically, for example, per driving scene, (1) the risk predictive function level with respect to the road shape, the attention function levels related to the concentration and the allocation, and the spatial attention function level can be detected on the basis of prediction control in the lateral direction that is calculated by the road model calculation, and (2) the risk predictive function levels with respect to the potential risk and the visible risk and the attention function levels related to the concentration and the allocation can be detected on the basis of prediction control in a vertical direction that is calculated by the road model calculation (see the upper portion of FIG. 6A). Here, the road shape prediction model is a model in which the future road shape is predicted, and may be stored in the storage section 300 in advance, or may be generated in the calculation processing section 100 based on the imaging data (target data) by the external cameras 61 and the radars 62 and the positional information detected by the position sensor 63.

For example, the predictive function level that is based on the behavior of the driver's sightline can be detected by a calculation using the driving scene recognized by the driving scene recognition section 210 and the behavior of the driver's sightline recognized by the sightline behavior detection section 412. More specifically, for example, (1) the attention function level related to the attention allocation during driving can be detected by calculating a matching degree between a point to be looked at and the driver's sightline per driving scene, (2) the risk predictive function levels with respect to the potential risk and the visible risk and the attention function level related to the attention allocation during driving can be detected by calculating, as a saliency index value, an area under the curve (AUC) value per driving scene, (3) the risk predictive function level with respect to the visible risk can be detected by calculating an amplitude of a saccade per driving scene, and (4) the risk predictive function level with respect to the potential risk and the attention function level related to the attention allocation during driving can be detected by calculating a frequency of the saccade per driving scene (see the upper portion of FIG. 6B).

For example, the predictive function level that is based on the behavior of the driver's head can be detected by a calculation using the driving scene recognized by the driving scene recognition section 210 and the behavior of the driver's head recognized by the head behavior detection section 411. More specifically, for example, (1) the attention function level related to the attention allocation during driving can be detected by calculating the cross-correlation between the head behavior and the external force on the basis of the behavior of the driver's head and the estimation result of the external force on the driver by the vehicle state sensor 64 per driving scene, and (2) the attention function level related to the attention allocation during driving can be detected by calculating eccentricity of a head position per driving scene (see the upper portion in FIG. 6B).

Base Function Detection Section

The base function detection section 435 detects the base function level based on the driving operation by the driver, the behavior of the driver's sightline, and/or the behavior of the driver's head, for example.

For example, the base function level that is based on the driving operation by the driver can be detected by a calculation using the driving scene recognized by the driving scene recognition section 210 and a pedal model (hereinafter also referred to as a pedal model calculation). More specifically, for example, a perceptual function level in the vertical direction and/or the motor function level of the foot can be detected per driving scene based on a feedback (FB) gain of the pedal, a delay in a pedal operation, performance of pedal control, and/or an estimation error between a model operation and an actual operation of the pedal (see a middle portion of FIG. 6A). Here, for example, in the pedal model, the accelerator pedal/brake pedal and a pedal support structure thereof are modeled. When data on a depression force that is associated with the accelerator operation/brake operation by the driver is input, thrust force data of an operation rod is output based on this depression force data.

In addition, for example, as the base function level that is based on the driving operation by the driver, the perceptual function level in the lateral direction and/or the motor function level of the hand can be detected per driving scene based on the feedback (FB) gain of the steering, a travel position, and/or the estimation error between the model operation and the actual operation of the steering wheel (see the middle portion of FIG. 6A). Here, the perceptual function level is an index that indicates a degree that the perceptual function is executed normally.

For example, the base function level that is based on the behavior of the driver's sightline can be detected by a calculation using the driving scene recognized by the driving scene recognition section 210 and the behavior of the driver's sightline recognized by the sightline behavior detection section 412. More specifically, for example, the perceptual function level regarding a range of vision can be detected per driving scene by calculating one or plural of (1) a bilateral difference between the saccades of the left eye and the right eye, (2) sightline distribution, and (3) the amount of nystagmus. In addition, the motor function level related to motion of the eyeballs can be detected per driving scene by calculating a speed of the saccade (see the middle portion in FIG. 6B).

For example, the predictive function level that is based on the behavior of the driver's head can be detected by a calculation using the driving scene recognized by the driving scene recognition section 210, the behavior of the driver's head recognized by the head behavior detection section 411, the behavior of the driver's sightline recognized by the sightline behavior detection section 412, and the recognition result by the driving operation recognition section 220. More specifically, for example, (1) the perceptual function levels related to the range of vision and the cognitive response time during driving as well as the motor function level related to the motion of the eyeballs can be detected by calculating the cross-correlation between the head behavior and the sightline behavior of the driver per driving scene, and (2) the motor function levels of the hand and the foot can be detected by calculating cross-correlation between the head behavior and a hand/foot function of the driver per driving scene (see the middle portion of FIG. 6B).

Abnormality Determination Section

The abnormality determination section 440 receives the involuntary function level calculated in the involuntary function detection section 420, the predictive function level calculated in the predictive function detection section 431, and the base function level detected by the base function detection section 435, comprehensively determines these, and thereby determines the driver abnormality.

More specifically, according to the driving scene that is recognized by the driving scene recognition section 210, the abnormality determination section 440 selects one or plural function levels from the involuntary function level, the predictive function level, and the base function level for use in the abnormality determination. In the case where the function level including the combination of the function levels match a specified condition, the abnormality determination section 440 determines that the driver is abnormal. For convenience of description, the function level that is selected according to the driving scene will be referred to as a target function level. For example, in the example of FIG. 4, the target function levels in the periods T11, T13, T21, T25, T31, T33 are the involuntary function level, the predictive function level, and the base function level. In addition, the target function levels in the periods T22, 124, T32 are the involuntary function level and the base function level. Furthermore, the target function level in the periods T12, T23 is the involuntary function level.

A type of the specified condition for the determination of the driver abnormality is not particularly limited. For example, a specified threshold may be provided for the calculated function level, and the determination may be made based on a comparison between the function level and the threshold. For example, an index, a reference model, or the like that serves as a reference may be prepared, and the driver abnormality may be determined based on a matching degree, divergence, or the like with such a reference or a reference model. A specific example thereof will be described below.

The specified condition may be stored in the storage section 300 in advance or may be able to be set from the outside of the vehicle A. Alternatively, the specified condition may be set for the one or plural function levels constituting the target function level. Furthermore, a level value of each of the function levels may be scored or added, or a weighted average of such values may be calculated to set the specified condition or reference for a total score of the entire target function level.

Moreover, the abnormality determination section 440 may determine that the sign of the driver abnormality is recognized in the case where the target function level matches the specified condition. Then, after the response checking section 450 checks the driver's response, the abnormality determination section 440 may finally determine the driver abnormality. That is, when determining the driver abnormality, the abnormality determination section 440 may make the determination in a stepwise manner including an inquiry to the driver.

Response Checking Section

The response checking section 450 has a function of checking the driver's response in the case where the abnormality determination section 440 determines that the sign of the driver abnormality is recognized. The response checking section 450 includes the inquiry section 451 and the response detection section 452.

The inquiry section 451 makes an inquiry to the driver when receiving an inquiry request to the driver from the abnormality determination section 440. This inquiry is made to check the driver's intention on whether the driver accepts emergency evacuation of the vehicle by the automated driving. For example, the inquiry is made by the voice via the speaker D2 or is displayed via the information display D1 such as the monitor.

The response detection section 452 detects the driver's response to the inquiry by the inquiry section 451. For example, the driver's response is made by operating the switch D3 or a speech using the microphone D4. When the driver's intention on the emergency stop can be checked, or when the driver's response is not made, the abnormality determination section 440 instructs the travel control section 500 to make the vehicle automatically evacuate to a road shoulder for a stop.

[Examples of Function Level Detection Processing and Abnormality Determination Processing in Each Stratum]

A description will hereinafter be made on detection action of the function level and abnormality determination action thereafter in each of the strata (action) including the involuntary action, the base action, and the predictive action by using a specific example. The following description will be made on an example of the detection operation of the function level in each of the strata to facilitate understanding of the embodiments and is not limiting. That is, a detection method other than that in the following description may be used to detect the function level in each of the strata.

<Detection Processing of Involuntary Function Level>

A description will herein be made on a detection operation example of the involuntary function levels related to the head behavior and the sightline behavior among the detection items of the involuntary function level related to the involuntary action illustrated in the lower portion of FIG. 6A and the lower portion of FIG. 6B with reference to the drawings.

Head Behavior

Figure 7:
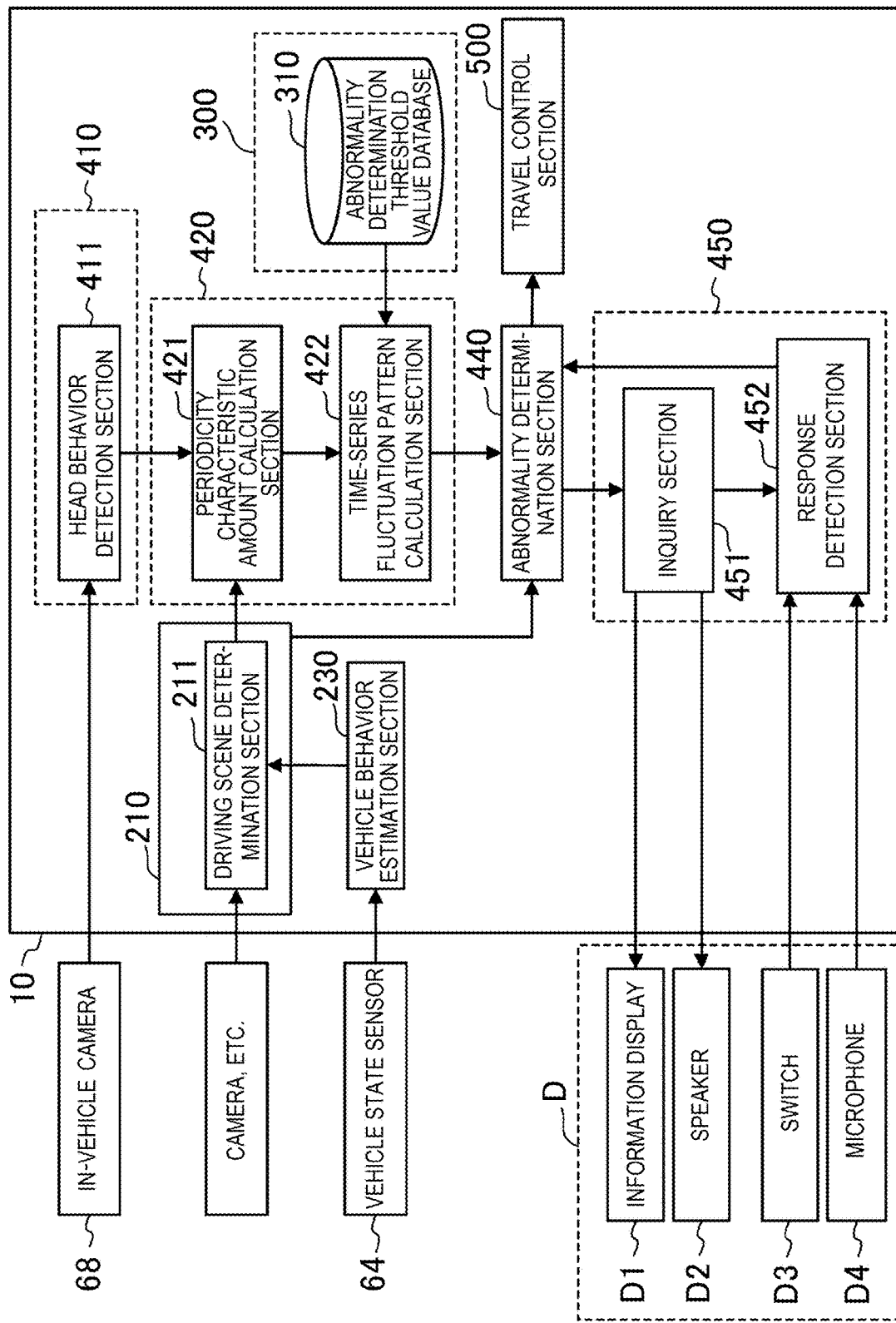
FIG. 7 is a block diagram for illustrating detection operation of an involuntary function level.

A description will be made on the detection operation example of the involuntary function level related to the head behavior with reference to FIG. 7 to FIG. 9. FIG. 7 is a block diagram for illustrating the detection operation of the involuntary function level. The blocks used for the description are extracted from the configuration illustrated in FIG. 5, and internal blocks are added when necessary.

More specifically, in the example of FIG. 7, the driving scene recognition section 210 includes a driving scene determination section 211. The involuntary function detection section 420 includes a periodicity characteristic amount calculation section 421 and a time-series fluctuation pattern calculation section 422. The response checking section 450 includes the inquiry section 451 and the response detection section 452. In addition, as described above, the driver behavior recognition section 410 includes the head behavior detection section 411.

In FIG. 7, the head behavior detection section 411 detects the behavior of the driver's head from the image captured by the in-vehicle camera 68. For example, the head behavior detection section 411 recognizes the driver's head from the image and calculates an inclination angle of the head, for example, a pitch angle and a roll angle thereof. The processing in the head behavior detection section 411 can be executed by the existing image processing technique.

Figure 9:
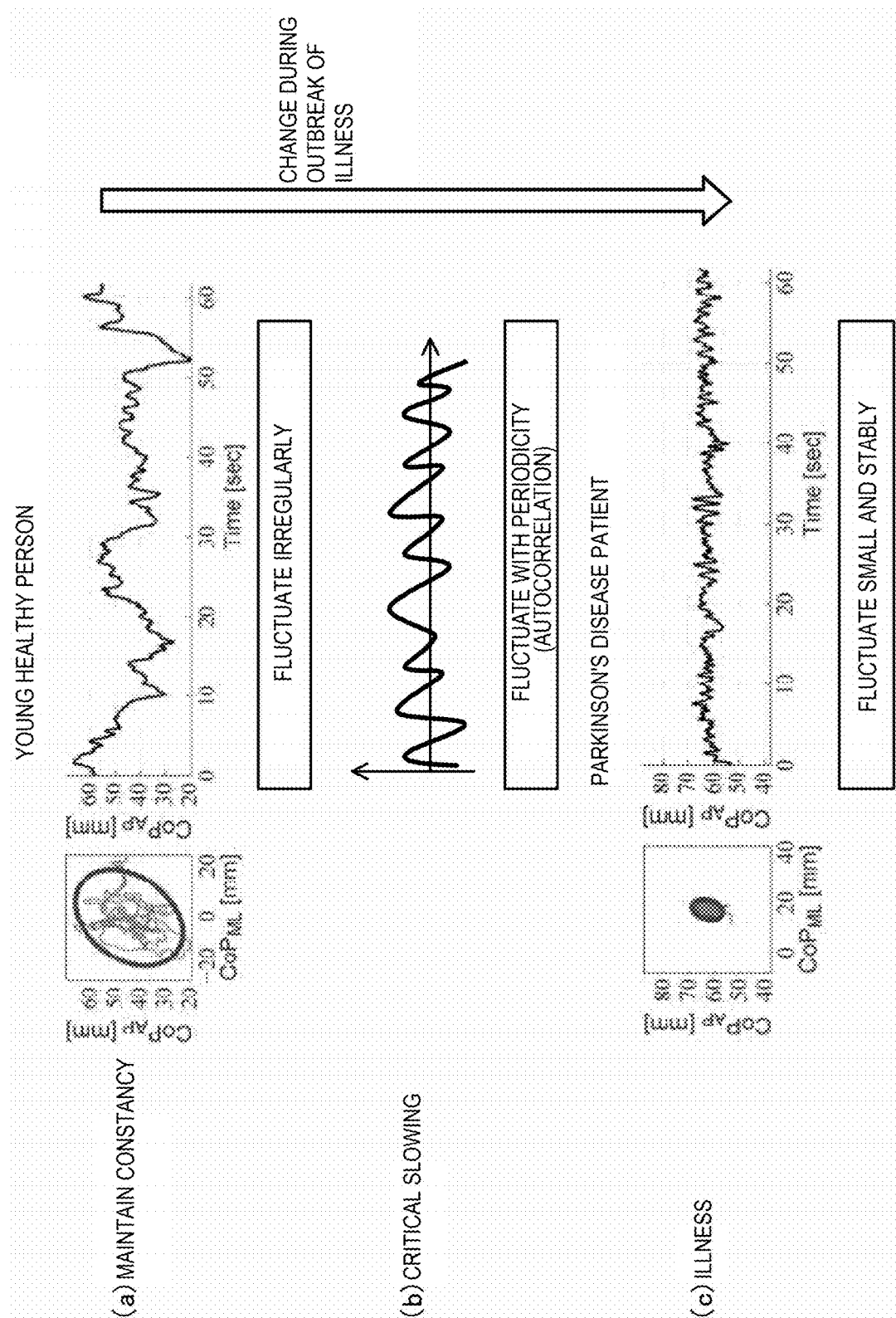
FIG. 9 is a view illustrating a relationship between constancy of behavior of the head and an illness, in which (a) illustrates a normal state, (b) illustrates a critical slowing state, and (c) illustrates a sick state.

FIG. 9 includes graphs, each of which illustrates a relationship between constancy of the head behavior and the illness (see Non-Patent document 2, 3). Each of the graphs in FIG. 9 represents the motion of the head that is seen from above, in which (a) represents the normal state where the constancy is maintained, (b) represents a state called critical slowing between the normal state and a sick state, and (c) represents the sick state. The graphs in FIGS. 9(*a*), (*c*) are cited from Non-Patent document 2.

The human has a function called consistency to keep a state being constant with respect to the disturbance. The consistency of the head behavior means a property that the driver tries to keep a head posture while driving. As illustrated in FIG. 9(*a*), in the normal state, the head fluctuates irregularly to keep the constancy. On the other hand, as illustrated in FIG. 9(*c*), in the sick state, the fluctuation of the head is reduced, and the behavior becomes stable. Then, as illustrated in FIG. 9(*b*), it is considered that, in the critical slowing state in transition from the normal state to the sick state, the head fluctuates with periodicity (autocorrelation) (see Non-Patent document 3).

Figure 8:
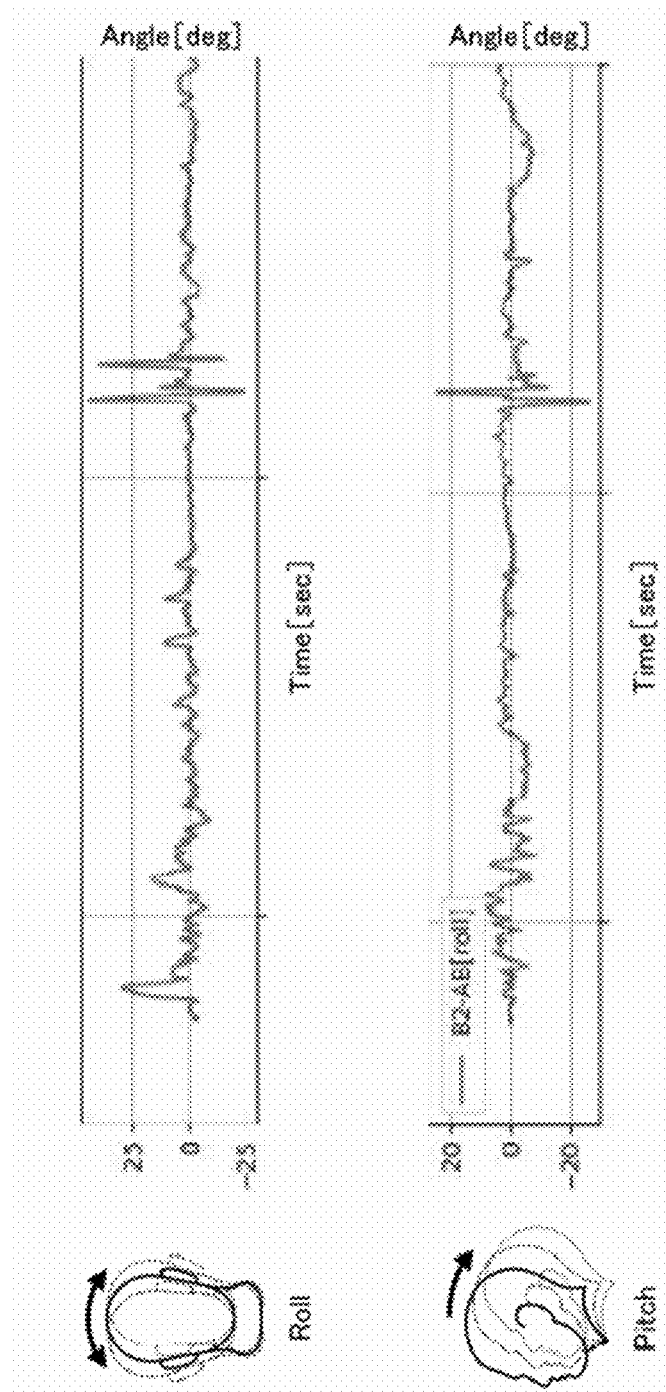
FIG. 8 illustrates examples of time-series data of a pitch angle and a roll angle of a head.

Thus, in this embodiment, time-series data on the head behavior as illustrated in FIG. 8 is acquired by the processing executed by the head behavior detection section 411. The time-series data on the head behavior is transmitted to the involuntary function detection section 420.

The driving scene determination section 211 determines whether the vehicle travel state corresponds to a scene where it is difficult to detect the sign of the driver abnormality, such as traveling at a corner, based on the driving scene recognized by the driving scene recognition section 210 and the vehicle behavior data received from the vehicle behavior estimation section 230. For example, the driving scene determination section 211 regards the acceleration in a right-left direction of the vehicle, which is indicated by the vehicle behavior data, as lateral acceleration applied to the driver's head, and determines whether such acceleration exceeds a specified value. In the case where the acceleration exceeds the specified value, the driving scene determination section 211 determines that it is currently in the scene where it is difficult to detect the sign of the driver abnormality. The determination result by the driving scene determination section 211 is transmitted to the involuntary function detection section 420.

The periodicity characteristic amount calculation section 421 calculates a periodicity characteristic amount from the time-series data on the head behavior acquired by the head behavior detection section 411. More specifically, for example, the periodicity characteristic amount calculation section 421 calculates, as the periodicity characteristic amount, an autocorrelation index (a scaling index a) by a detrended fluctuation analysis (DFA). In addition, when the driving scene determination section 211 determines that it is currently in the scene where it is difficult to detect the sign of the driver abnormality, the periodicity characteristic amount calculation section 421 does not calculate the periodicity characteristic amount.

The time-series fluctuation pattern calculation section 422 divides time-series data on the periodicity characteristic amount, which is acquired by the periodicity characteristic amount calculation section 421, in time order, calculates a time-series fluctuation pattern from the divided time-series data, and categorizes the patterns. More specifically, for example, the time-series fluctuation pattern calculation section 422 reduces a dimension of the time-series data on the periodicity characteristic amount by using UMAP as a non-linear dimension compression method, and converts the time-series data into two-dimensional data. Then, the time-series fluctuation pattern calculation section 422 compares the data acquired by this two-dimensional data conversion with the threshold in an abnormality determination threshold database 310 stored in the storage section 300, calculates the involuntary function level based on the comparison result, and outputs the involuntary function level to the abnormality determination section 440. For example, a determination line LTH in a two-dimensional map illustrated in FIG. 10 corresponds to the threshold stored in the abnormality determination threshold database 310. The time-series fluctuation pattern calculation section 422 calculates the involuntary function level based on which side of the determination line LTH the data acquired by the two-dimensional data conversion is located and how far such data is separated from the determination line LTH. The determination line LTH is an example of a determination criterion.

Sightline Behavior

Figure 11:
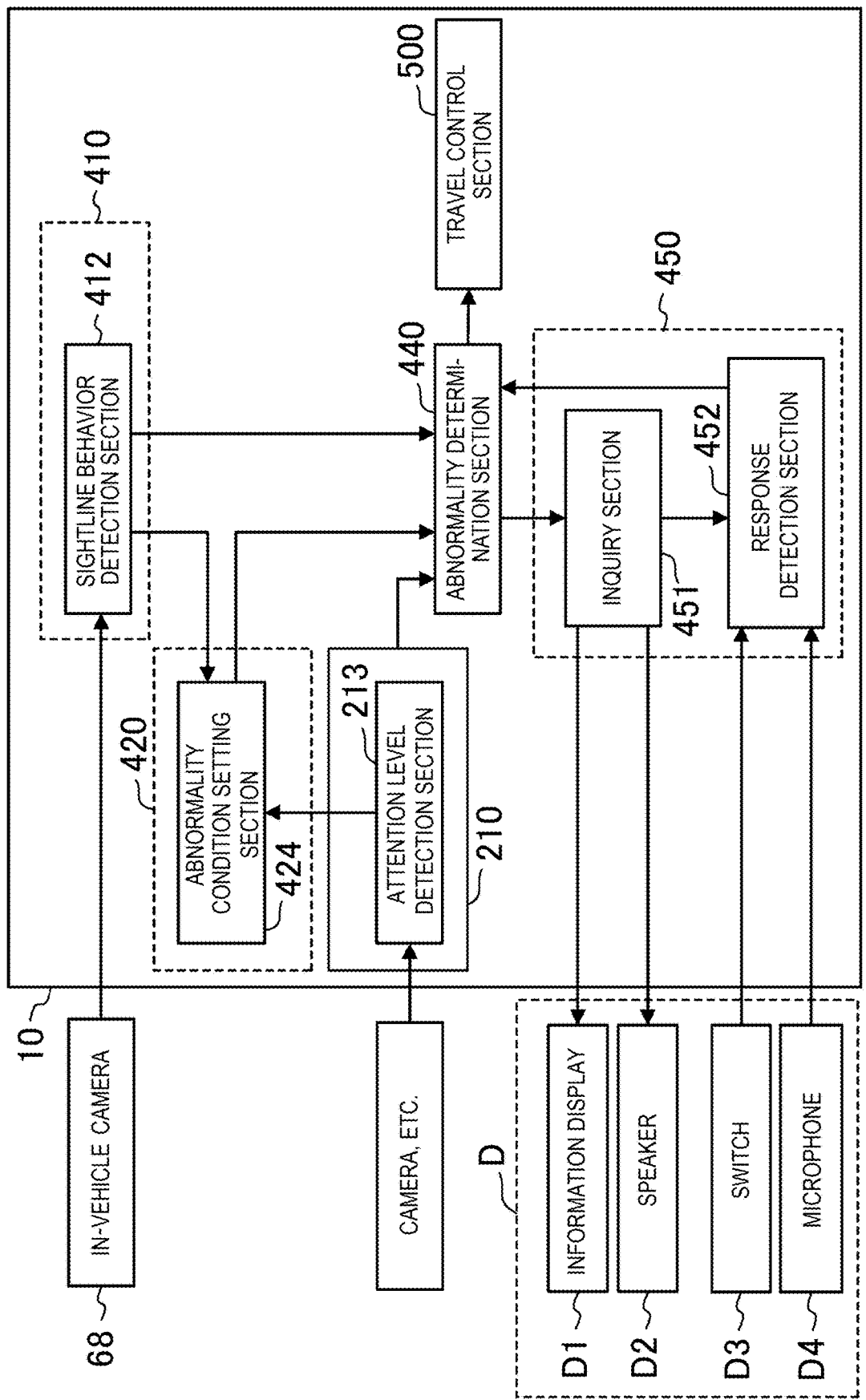
FIG. 11 is a block diagram for illustrating the detection operation of the involuntary function level.

A description will be made on a detection operation example of the involuntary function level related to the sightline behavior with reference to FIG. 11 to FIG. 13. FIG. 11 is a block diagram for illustrating the detection operation of the involuntary function level. The blocks used for the description are extracted from the configuration illustrated in FIG. 5, and internal blocks are added when necessary. More specifically, in the example of FIG. 11, the driving scene recognition section 210 includes an attention level detection section 213. The involuntary function detection section 420 includes an abnormality condition setting section 424. In addition, as described above, the driver behavior recognition section 410 includes the sightline behavior detection section 412. The response checking section 450 includes the inquiry section 451 and the response detection section 452.

Figure 10:
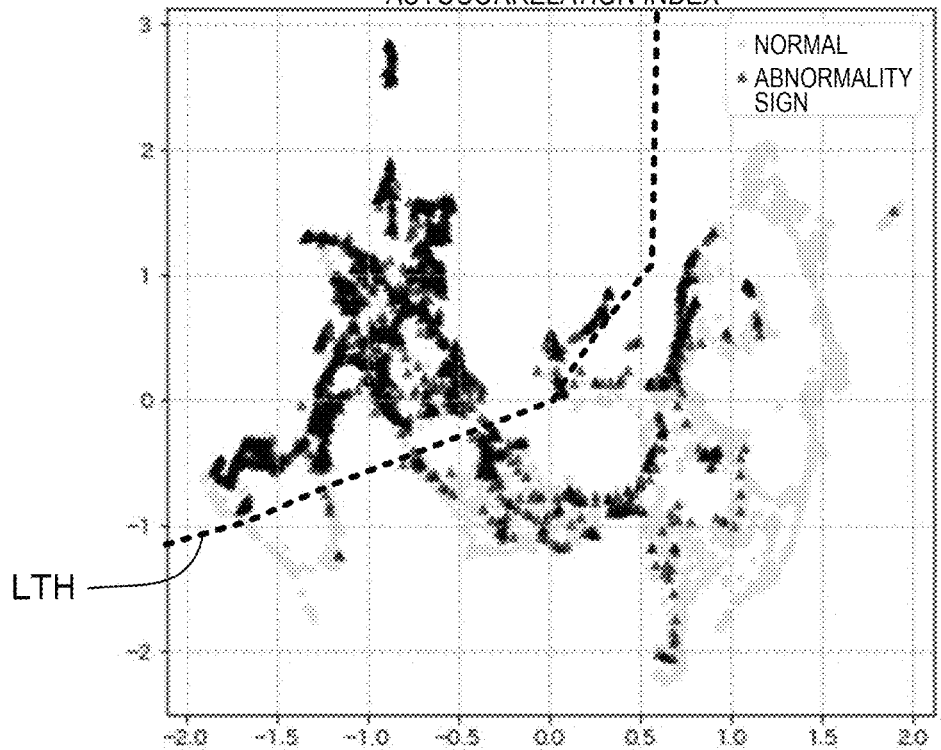
FIG. 10 is a graph illustrating a classification result of time-series fluctuation patterns of an autocorrelation index.

In FIG. 10, the sightline behavior detection section 412 calculates the behavior of the driver's sightline (for example, a saccade) from the image captured by the in-vehicle camera 68. The saccade is saccadic motion of the eyeballs occurred when the person (for example, the driver) intentionally moves the sightline. More specifically, the saccade is the motion of the eyeballs to move the sightline from a focus point at which the sightline stays for a specified time to a next focus point. In this example, the sightline behavior detection section 412 executes the sightline detection processing on the image data acquired by the in-vehicle camera 68, to detect the driver's sightline and detect the saccade of the driver on the basis of movement of the driver's sightline. This sightline detection processing may be processing that is executed by using a learning model generated by deep learning (a learning model for detecting the sightline), or may be processing that is executed by using a well-known sightline detection technique.

The attention level detection section 213 detects an attention level in the external environment of the vehicle by using the data that is acquired by one or plural of the external cameras 61, the radars 62, the position sensor 63, the external communication device 65, and the vehicle behavior estimation section 230. The attention level is an index that indicates the number of attention points (attention points to be checked by the driver of the vehicle during the travel) in the exterior environment of the vehicle. As the number of the attention points is increased in the external environment of the vehicle, the attention level in the external environment of the vehicle is increased. The detection result by the attention level detection section 213 is transmitted to the abnormality condition setting section 424. Examples of the attention point are a point where running of an object into the road is predicted and a point where the object that can be the obstacle for the host vehicle exists.

The abnormality condition setting section 424 sets an abnormality condition that is used for the determination on the driver abnormality by the abnormality determination section 440. In this example, the abnormality condition setting section 424 sets a threshold included in the abnormality condition based on the saccade of the driver detected by the sightline behavior detection section 412.

(Detection Processing of Amplitude of Saccade)

Next, a description will be made on operation of the abnormality determination section 440 herein with reference to FIG. 12.

Figure 12:
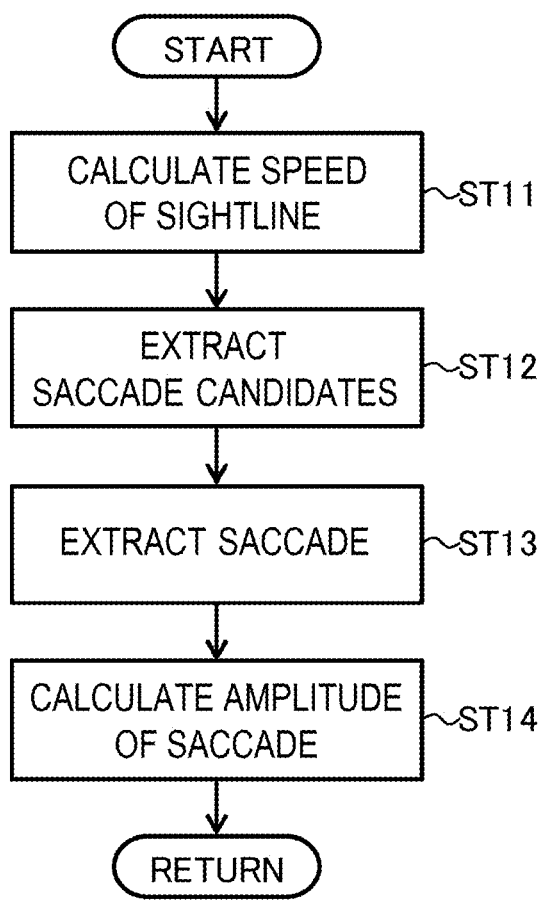
FIG. 12 is a flowchart for illustrating saccade detection processing.

First, the sightline behavior detection section 412 sets a first period P1 in which the amplitude of the saccade is detected, and executes processing illustrated in FIG. 12 (steps ST11 to ST14) every time the first period P1 is set.

—Step ST11—

The sightline behavior detection section 412 detects the driver's sightline. For example, the sightline behavior detection section 412 detects the driver's pupils from the image (the image data) acquired by the in-vehicle camera 68, and detects the driver's sightline based on the detected pupils. Then, the sightline behavior detection section 412 calculates, from the driver's sightline, a speed of the driver's sightline based on a temporal change in a moving distance of the driver's sightline.

—Step ST12—

Next, the sightline behavior detection section 412 extracts a saccade candidate that is a candidate for the saccade based on a moving speed of the sightline. For example, the sightline behavior detection section 412 extracts, as a "gaze period", a period in which a state where the moving speed of the sightline is lower than a predetermined speed threshold (for example, 40 deg/s) continues for a predetermined stagnation time (for example, 0.1 second). Then, of the movement of the sightline in a period between the two adjacent gaze periods, the sightline behavior detection section 412 extracts, as the "saccade candidate", the movement of the sightline, the speed of which is equal to or higher than the speed threshold (for example, 40 deg/s), and the moving distance of which is equal to or longer than a predetermined distance threshold (for example, 3 deg).

—Step ST13—

Next, the sightline behavior detection section 412 derives a regression curve, which is based on the plural saccade candidates, by a method of least squares, draws a reference curve in each of increased/reduced directions of the moving speed of the sightline with respect to the regression curve, and sets a portion between the reference curves as a saccade range. Then, of the plural saccade candidates, the sightline behavior detection section 412 extracts, as the saccade, the saccade candidate included in the specified saccade range, but does not extract, as the saccade, the saccade candidate not included in the saccade range.

—Step ST14—

Next, the sightline behavior detection section 412 calculates an amplitude ds of the saccade in the first period P1. More specifically, the sightline behavior detection section 412 calculates an average value of the amplitudes ds of the saccade included in the first period P1 as the "amplitude ds of the saccade in the first period P1".

Experiment 1 Conducted by Inventors of the Present Application

The inventors of the present application conducted an experiment as follows to examine a relationship between the driver state and the behavior (particularly, the motion of the sightline) of the driver.

First, to collect data on a sudden abnormal state, a patent having a symptom of epilepsy (hereinafter described as an "epilepsy patent") was selected as a subject. Then, the subject spuriously experienced the driving operation of the vehicle by using a driving simulator 70 (see FIG. 20). More specifically, the subjects watched a video during the travel of the vehicle (a video that showed the external environment of the vehicle seen from the inside of the vehicle) by using the driving simulator 70, and behavior of the subjects during the experiment was observed. In this way, the behavior of the subjects while driving the vehicle was spuriously observed. In this experiment, a camera was installed in front of the subject who watched the video during the travel of the vehicle, and the camera was set such that the subject's eyeballs were included in an imaging area.

Then, the sightline detection processing was executed on image data acquired by the camera, and the subject's sightline was thereby detected. In addition, the subject's sightline, which was acquired by the sightline detection processing, was subject to saccade detection processing. In this way, the saccade of the subject was detected, and the amplitude of the saccade in a specified period was calculated. These types of the processing are the same as the processing executed by the sightline behavior detection section 412.

The experiment described so far was conducted for the plural subjects. Of these plural subjects, there was a subject who had an attack of epilepsy during the experiment. Thus, data on the subject during the attack of the epilepsy could be acquired.

Figure 13:
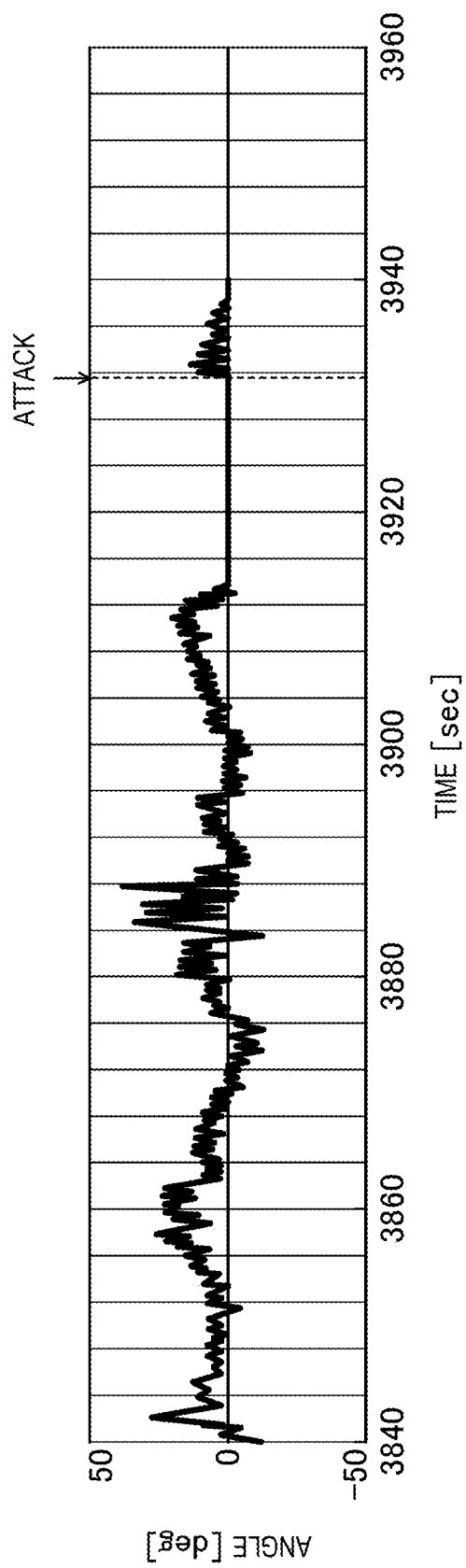
FIG. 13 is a graph illustrating movement of a sightline when an epilepsy patient has a stroke.

As illustrated in FIG. 13, in a period (approximately 3915 seconds to approximately 3930 seconds in FIG. 13) from a period immediately before onset of the attack of epilepsy to a time point at which the attack of epilepsy occurred, the amplitude and a frequency of the saccade of the subject were further reduced to zero. This state where the amplitude and the frequency of the saccade of the subject continues for 10 seconds or longer.

For example, the abnormality determination section 440 stores the amplitude ds of the saccade in the first period P1, in which the driver state is the normal state, in the storage section 300, and sets a threshold for a saccade amplitude abnormality determination at 50% of the amplitude (for example, an average value) in the normal state. Then, for example, when the amplitude ds of the saccade of the driver becomes equal to or smaller than the threshold for a specified period in a consecutive manner, the abnormality determination section 440 determines that the driver is abnormal.

Abnormality Determination Processing

As described above, the target function level in the periods T12, T23 is only the involuntary function level. Thus, in the periods T12, T23, the abnormality determination section 440 determines the driver abnormality based on the involuntary function level that is output from the involuntary function detection section 420. At this time, the evaluation items to be used and a combination thereof are not particularly limited. For example, in the case where the evaluation items as those illustrated in FIGS. 6A, 6B are present, the items to be used may be selected according to the driving scene in which the vehicle A travels. For example, as illustrated in FIG. 14, a table in which indices that can be evaluated are linked to the driving scene may be prepared. Then, the driver abnormality may be determined by combining the items that can be used for the determination. In FIG. 14, indices "OPERATION", "HEAD", and "SIGHTLINE" respectively correspond to the items "OPERATION", "HEAD", and "SIGHTLINE" in FIGS. 6A, 6B. In addition, in FIG. 14, a "circle" indicates the item that can be used for the abnormality determination, and "–" indicates the item, use of which for the abnormality determination is difficult. Furthermore, C in FIG. 14 is added with a reference numeral according to a reason for the difficulty. C1 indicates that action corresponding to the determination target is not performed. C2 indicates that a difference in action between an abnormal time and a normal time hardly occurs at a stage of the sign. C3 indicates that disturbance is significant.

Then, in the case where the driver abnormality is confirmed, the travel control section 500 is instructed to execute control for making the vehicle A automatically evacuate to the road shoulder for the stop. As described above, when making the abnormality determination, the abnormality determination section 440 may check the driver's response via the response checking section 450 and then finally determine the driver abnormality.

<Detection Processing of Base Function Level>

A description will herein be made on a detection operation example of the base function level related to the driving operation among the detection items of the base function level related to the base action illustrated in the middle portion of FIG. 6A and the middle portion of FIG. 6B with reference to the drawings.

Driving Operation

Figure 15:
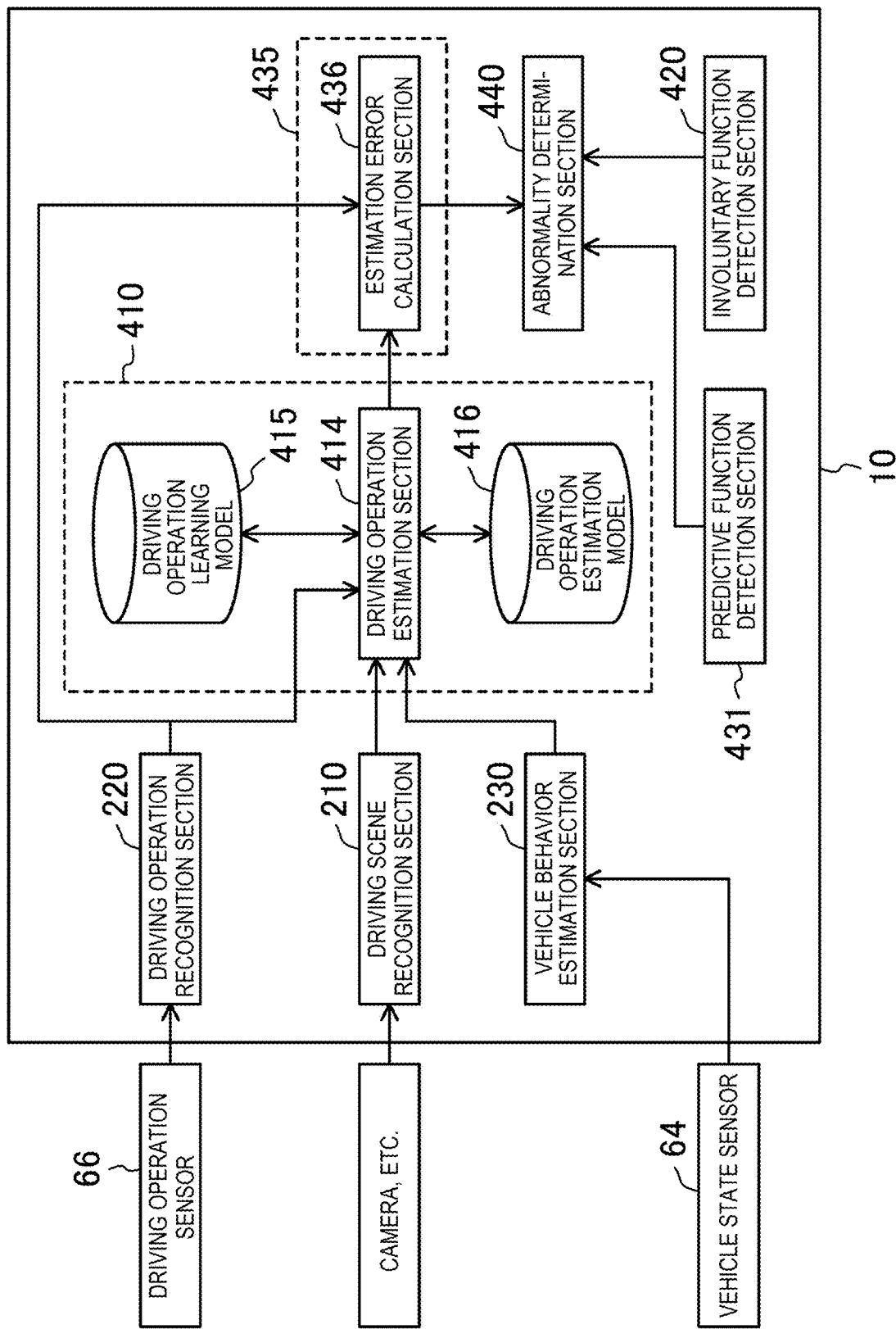
FIG. 15 is a block diagram for illustrating detection operation of a base function level.

FIG. 15 is a block diagram for illustrating the detection operation of the base function level. The blocks used for the description are extracted from the configuration illustrated in FIG. 5, and internal blocks are added when necessary. More specifically, in the example illustrated in FIG. 15, the driver behavior recognition section 410 includes the driving operation estimation section 414, a driving operation learning model 415, and a driving operation estimation model 416. The base function detection section 435 includes an estimation error calculation section 436. For example, the driving operation learning model 415 and the driving operation estimation model 416 are stored in the storage section 300.

In FIG. 15, the driving operation estimation section 414 receives the driving operation information recognized by the driving operation recognition section 220, the driving scene information recognized by the driving scene recognition section 210, and the vehicle behavior data generated by the vehicle behavior estimation section 230. For example, the driving scene information includes information on the traveling lane, information on a speed limit, and the positional information of the vehicle. Meanwhile, as described above, the vehicle behavior data includes the vehicle speed information. During the travel of the vehicle A, the driving operation estimation section 414 uses the driving operation learning model 415, which is generated by deep learning, to generate and accumulate a model parameter indicative of a driving characteristic of the normal driving operation by the driver from the driving operation information, the driving scene information, and the vehicle behavior data described above.

Furthermore, during the travel of the vehicle A, the driving operation estimation section 414 uses the driving operation estimation model 416, which is generated by deep learning, to estimate the driving operation by the driver of the moment from the driving operation information, the driving scene information, and the vehicle behavior data, and the model parameter described above. That is, the driving operation estimation section 414 estimates, from the usual driving operation by the driver, what type of the driving operation the driver will perform in the normal state (the healthy state) in the driving scene of the moment. The driving operation estimation section 414 outputs an estimation value of the driving operation (hereafter referred to as an operation estimation value) to the estimation error calculation section 436.

Figure 16A:
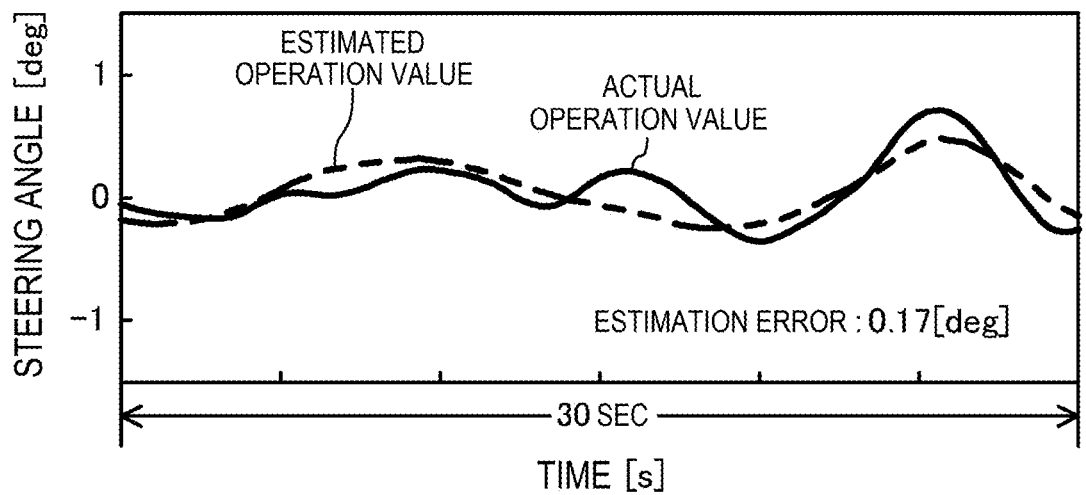
FIG. 16A and FIG. 16B include graphs in each of which steering operations of in a normal state and an abnormal state.
Figure 16B:
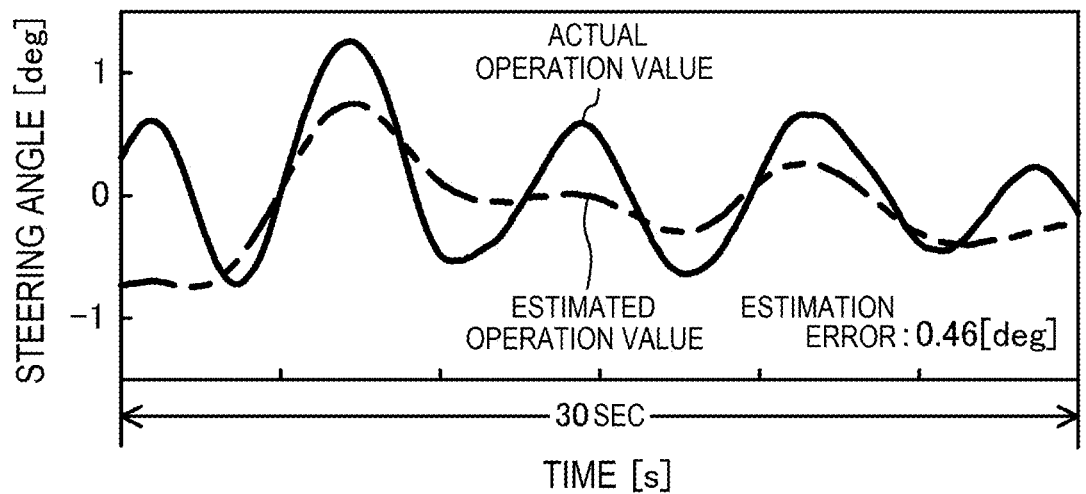

The estimation error calculation section 436 compares the operation estimation value to a value that is based on the actual driving operation (hereinafter referred to as an actual operation value), calculates a degree of deviation from the usual operation, and outputs the degree of the deviation as an operation deviation degree to the abnormality determination section 440. In FIGS. 16A and 16B, regarding the steering operation, the operation estimation value and the actual operation value are illustrated in an overlapping manner for each of the steering operation in the normal state and the steering operation in the abnormal state, respectively. FIGS. 16A and 16B illustrate 30 seconds of driving data in the driving scene in each of the normal state and the abnormal state, respectively.

The abnormality determination section 440 determines the sign of the driver abnormality based on whether the operation deviation degree, which is received from the estimation error calculation section 436, satisfies a specified criterion. Although a method for setting the specified criterion is not particularly limited, for example, such a criterion is set that it is determined that there is the sign of the driver abnormality in the case where, as the steering operation deviation degree, an average of the steering estimation errors in the specified period (30 seconds in FIG. 16) is equal to or higher than 0.4 [deg]. Alternatively, instead of providing the simple threshold, a divergence score that is based on a divergence amount from the steering estimation error may be calculated, and the base function level may be calculated based on the divergence score.

Abnormality Determination Processing

As described above, the target function levels in the periods T22, T24, T32 in FIG. 4 are the base function level and the involuntary function level. Thus, in the periods T22, 124, T32, the abnormality determination section 440 determines whether the involuntary function level, which is output from the involuntary function detection section 420, and the base function level, which is output from the base function detection section 435, including the combination thereof match a specified condition. In this case, as illustrated in FIG. 14 described above, the combination of the indices may be determined according to the driving scene. Alternatively, the level value of each of the function levels may be scored or added, or the weighed average of such values may be calculated to set the specified condition for the total score including some or all of the scores selected from the base function level and the involuntary function level.

Figure 17:
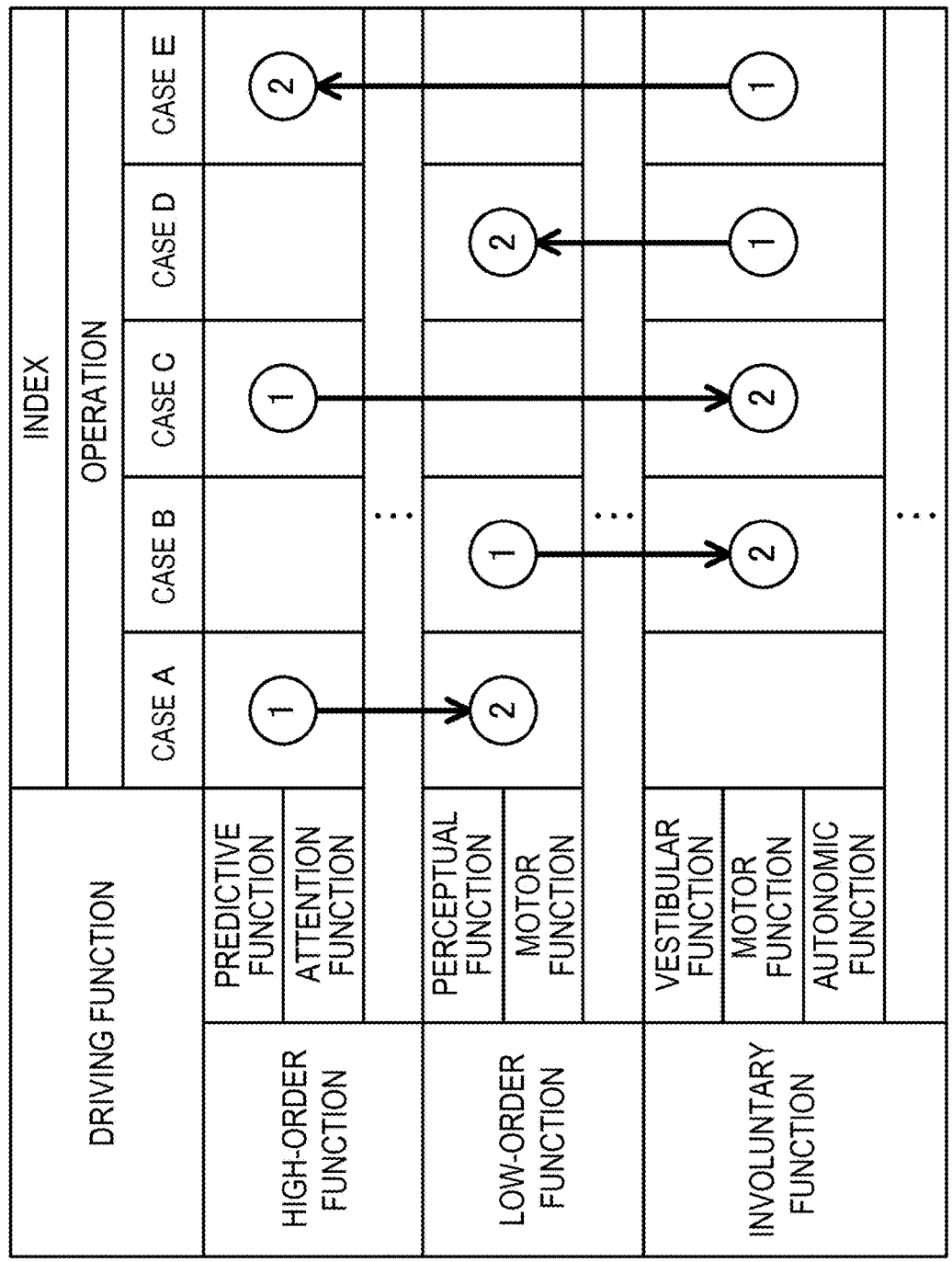
[FIG. 17]

As illustrated in FIG. 17, there is a case where the declining order of the function is known according to the type of the illness or the like. In such a case, the specified condition may be set stepwise in consideration of the declining order of the function. Then, the driver abnormality may be determined by determining whether the function level matches the set condition.

For example, CASE B in FIG. 17 is a case where the involuntary function is declined after the decline of the base function. An example that corresponds to such a case is that impairment of the motor functions of the hands and feet is developed due to infarction of thalamus or the like, is further progressed to cause a posture keeping difficult state (for example, of an unbalanced trunk, or the like). In this case, the decline in the base function level related to the driving operation is detected. Thereafter, instability of the head behavior appears. That is, the decline in the involuntary function level is detected. Accordingly, in consideration of this order, when the base function level is declined to be equal to or lower than the specified determination criterion, the abnormality determination section 440 may lower the determination threshold for the involuntary function level, to facilitate the abnormal determination of the involuntary function level. The determination threshold of the involuntary function level is an example of the determination criterion.

For example, CASE D in FIG. 17 is a case where the base function is declined after the decline of the involuntary function. As such a case, for example, there is a case where the head behavior becomes unstable in the driving scene as that in the period T23 to T24 in FIG. 4 (a situation where the determination accuracy of the involuntary function level seems to be higher than that of the base function level). That is, from the knowledge of the inventors, in the case where the driver suffers from the illness, the function related to the high-order action started being declined first, and thereafter, the decline in the function related to the base action and the decline in the function related to the involuntary action sequentially occur. However, in the driving scene as that in the periods T23 to T24 in FIG. 4, there is a case where the sign of the abnormality of the involuntary function is detected before the detection of the driving function. Thus, in such a case, when the involuntary function detection section 420 detects that the head behavior becomes unstable, the abnormality determination section 440 may lower the determination threshold for the base function level used by the driving function detection section 430. In this way, the abnormality of the base function level on a curved road or the like thereafter is more likely to be determined. As a result, it is possible to simultaneously discover the driver abnormality early and make the determination with a high degree of accuracy. At this time, the instability of the head behavior and the determination threshold of the base function level are examples of the determination criteria.

<Detection Processing of Predictive Function Level>

A description will herein be made on a detection operation example of the base function levels related to the sightline behavior and the driving operation among the detection items of the predictive function level related to the base action illustrated in the upper portion of FIG. 6A and the upper portion of FIG. 6B with reference to the drawings.

Sightline Behavior and Driving Operation

A block diagram having a similar configuration to FIG. 11 can be used for the detection operation of the predictive function level related to the sightline behavior. Thus, a description herein will be centered on different points from the detection operation of the involuntary function level. More specifically, the base function detection section 435 is provided at the position of the involuntary function detection section 420 in FIG. 11.

The sightline behavior detection section 412 herein calculates a direction of the driver's sightline from an image of the driver's eyeballs captured by the in-vehicle camera 68. For example, the sightline behavior detection section 412 sets a state where the driver looks at a lens of the in-vehicle camera 68 as a reference, detects a change in the driver's pupils from the reference, and thereby calculates the direction of the driver's sightline. The sightline direction calculated by the sightline behavior detection section 412 is transmitted to the predictive function detection section 431. Similarly, the driving scene recognized by the driving scene recognition section 210 is transmitted to the predictive function detection section 431.

In the predictive function detection section 431, processing to superpose the sightline, which is calculated by the sightline behavior detection section 412, onto the driving scene recognized by the driving scene recognition section 210 is performed.

Experiment 2 Conducted by Inventors of the Present Application

Figure 18:
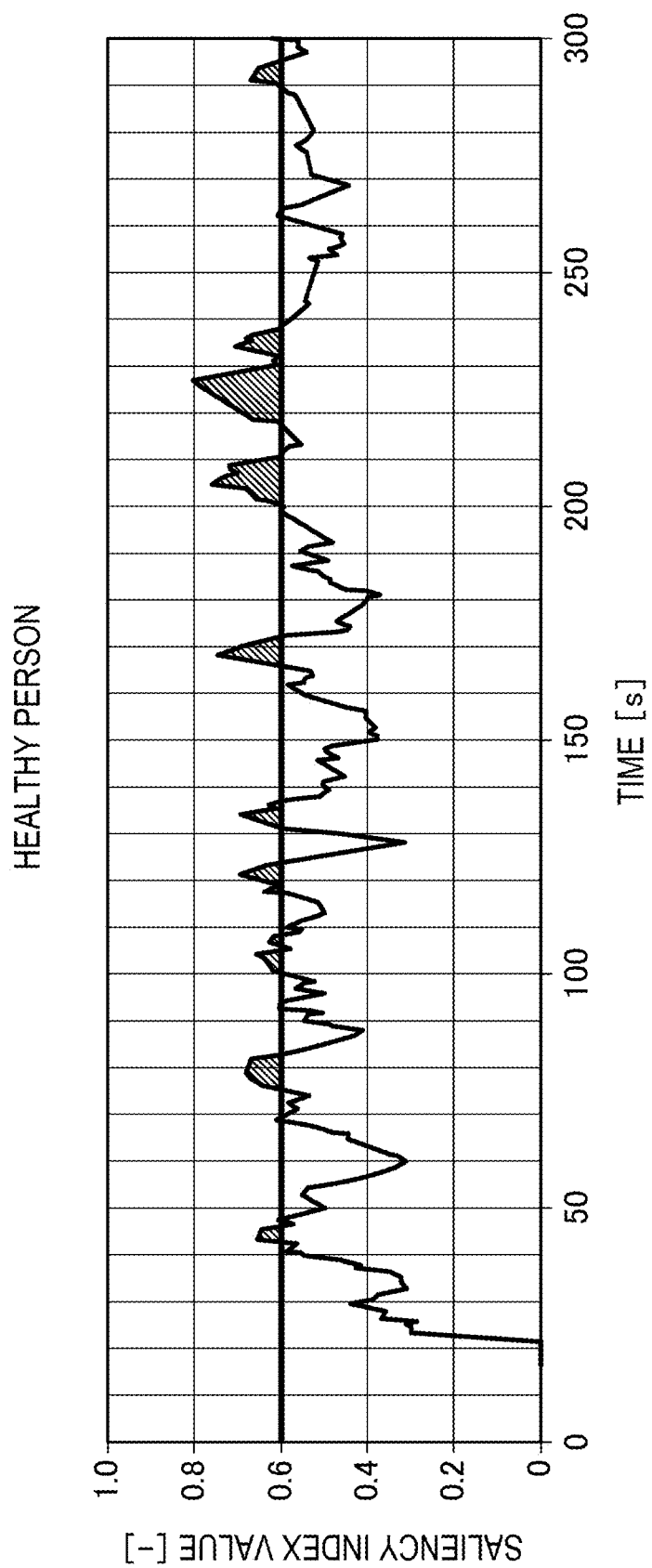
FIG. 18 is a graph exemplifying a change in a saliency index value of a healthy person.
Figure 19:
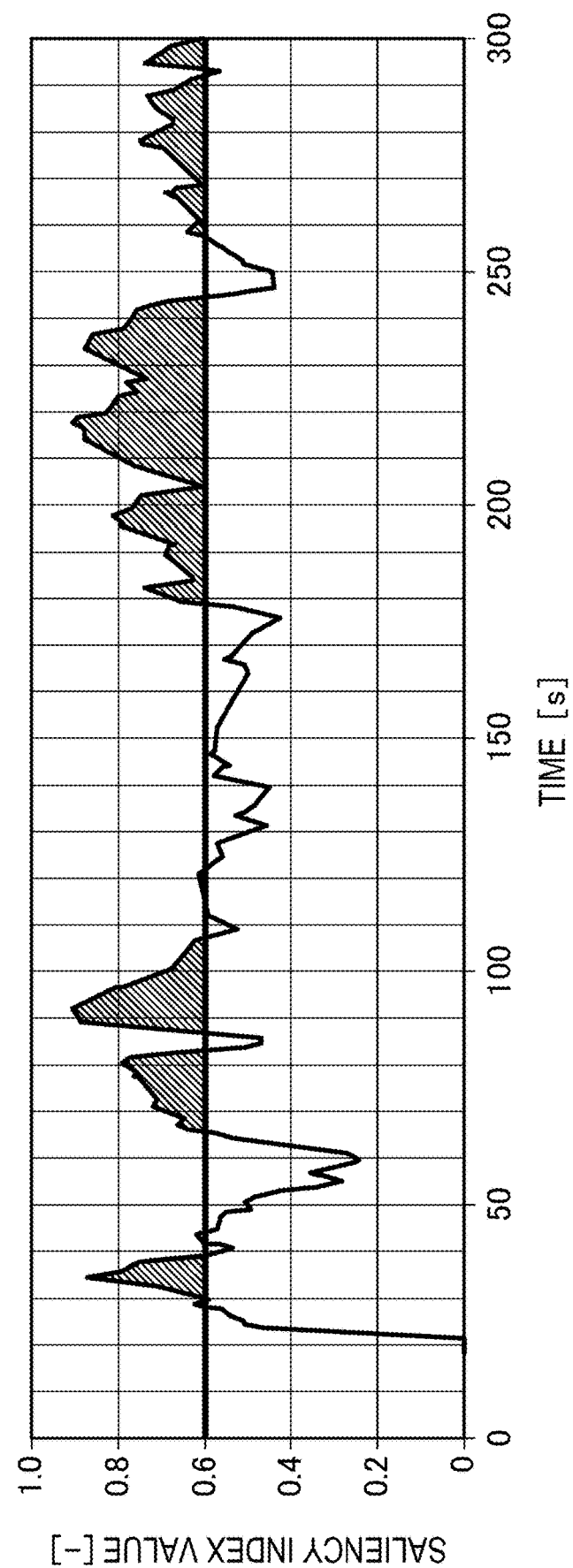
FIG. 19 is a graph exemplifying a change in a saliency index value of an attention impairment patent.

In each of FIGS. 18 and 19, the driver's sightline is detected by using the driving simulator 70 and is plotted as a temporal change in a saliency index. FIG. 18 illustrates a measurement result of the healthy person, and FIG. 19 illustrates a measurement result of the dysfunction patient. Since the travel speeds differ from each other, time axes and travel positions do not always match.

The saliency index is an index, a numerical value of which is increased with an increase in noticeability of a high saliency area.

In the examples illustrated in FIGS. 18 and 19, for example, the abnormality condition setting section 424 sets, as a specified condition, a threshold at 0.6 where the noticeability of the high saliency area is determined to be relatively high, and sets an area where the saliency index exceeds the threshold with respect to a specified time. In such a case, in the case where the area (an area of a region diagonal lines) where the saliency index exceeds 0.6 exceeds the specified threshold, the abnormality determination section 440 determines that the driver is abnormal (for example, suffers from the attention dysfunction) or has the sign of the abnormality. That is, the abnormality determination section 440 determines that the driver is abnormal or has the sign of the abnormality.

Experiment 3 Conducted by Inventors of the Present Application

Figure 20:
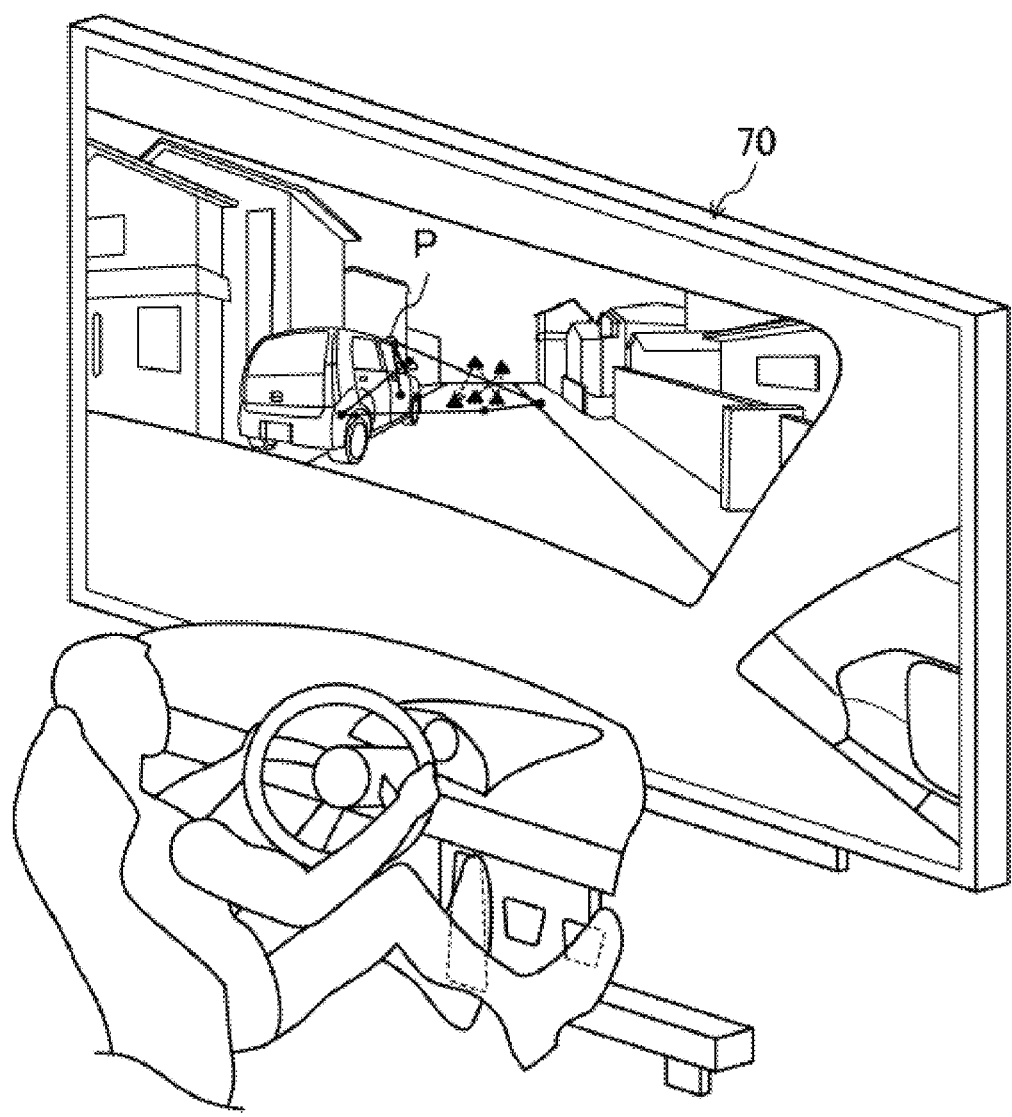
FIG. 20 is a view illustrating an example of an experiment result by a driving simulator.
Figure 21:
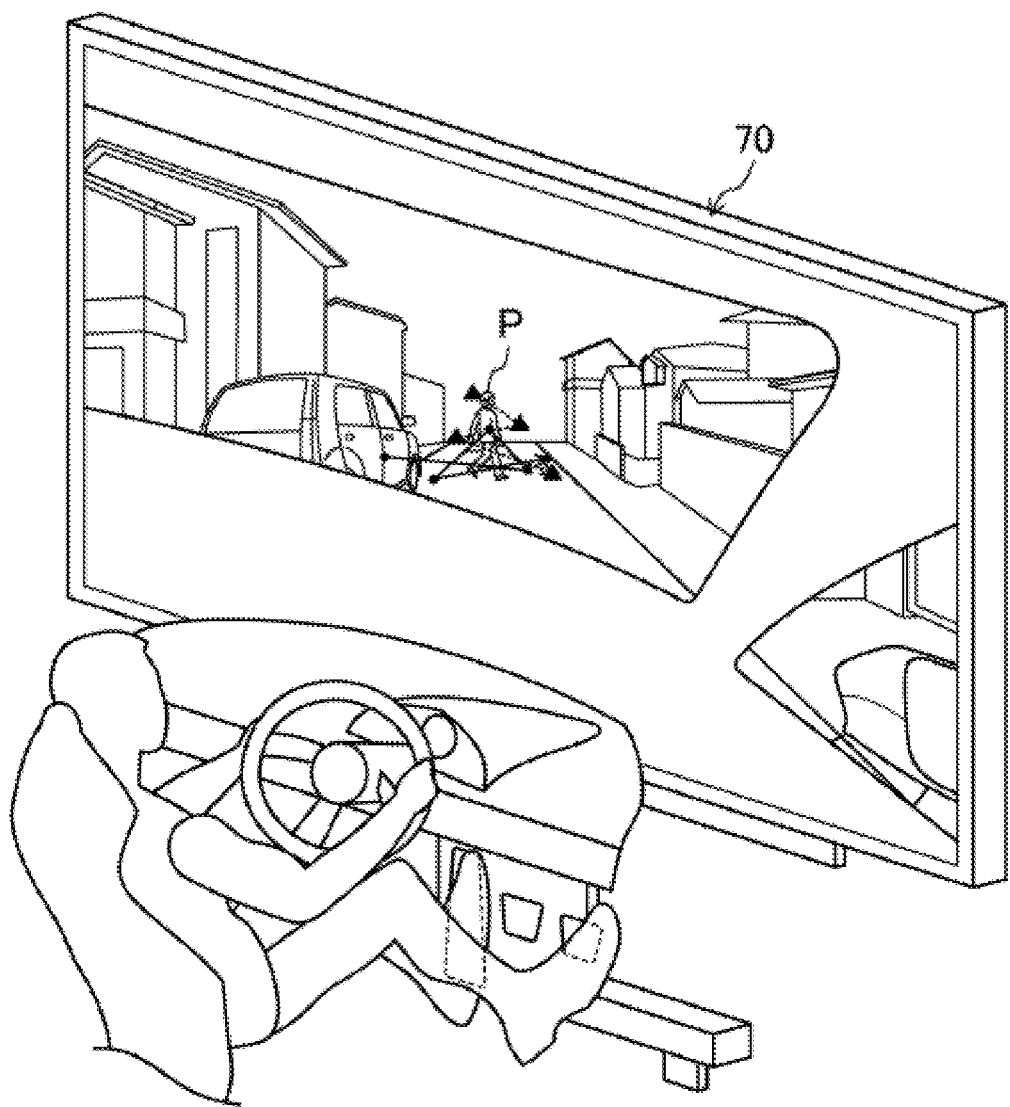
FIG. 21 is a view illustrating an example of the experiment result by the driving simulator.

In each of FIGS. 20 and 21, the driver's sightline is detected by using the driving simulator 70, and a result of superposition of the driver's sightline on the image of the driving scene is illustrated. The similar processing is executed by the predictive function detection section 431.

Figure 22A:
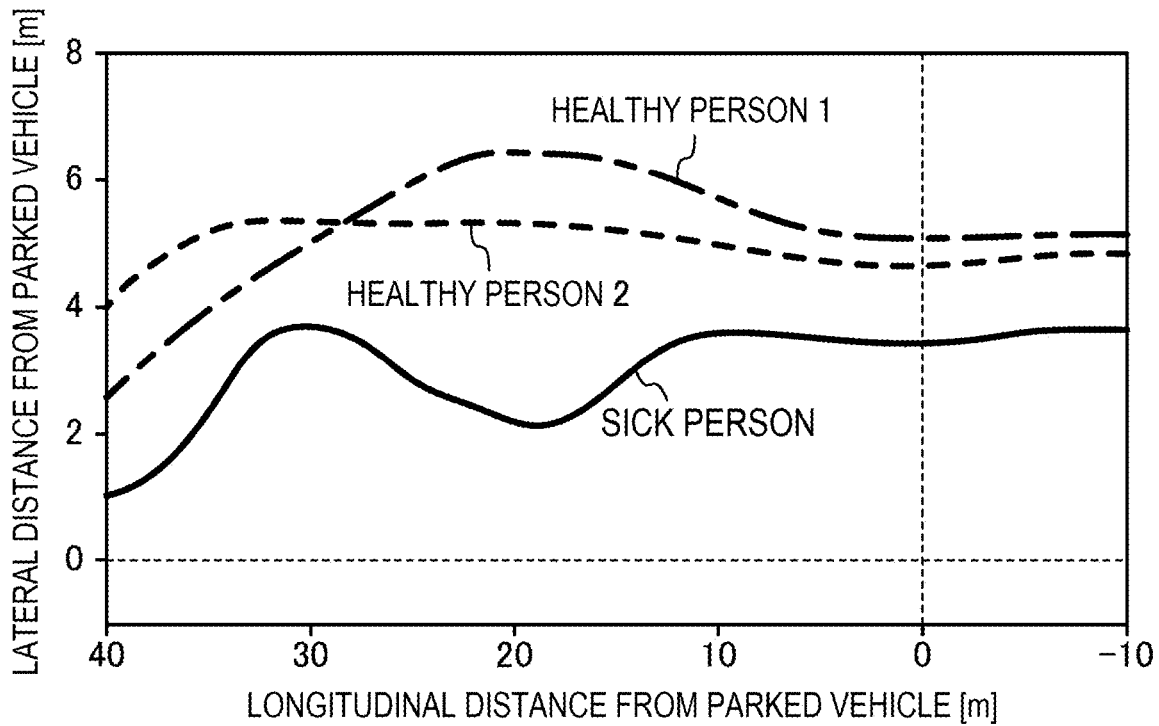
FIGS. 22A and 22B illustrate examples of the experiment result by the driving simulator.
Figure 22B:
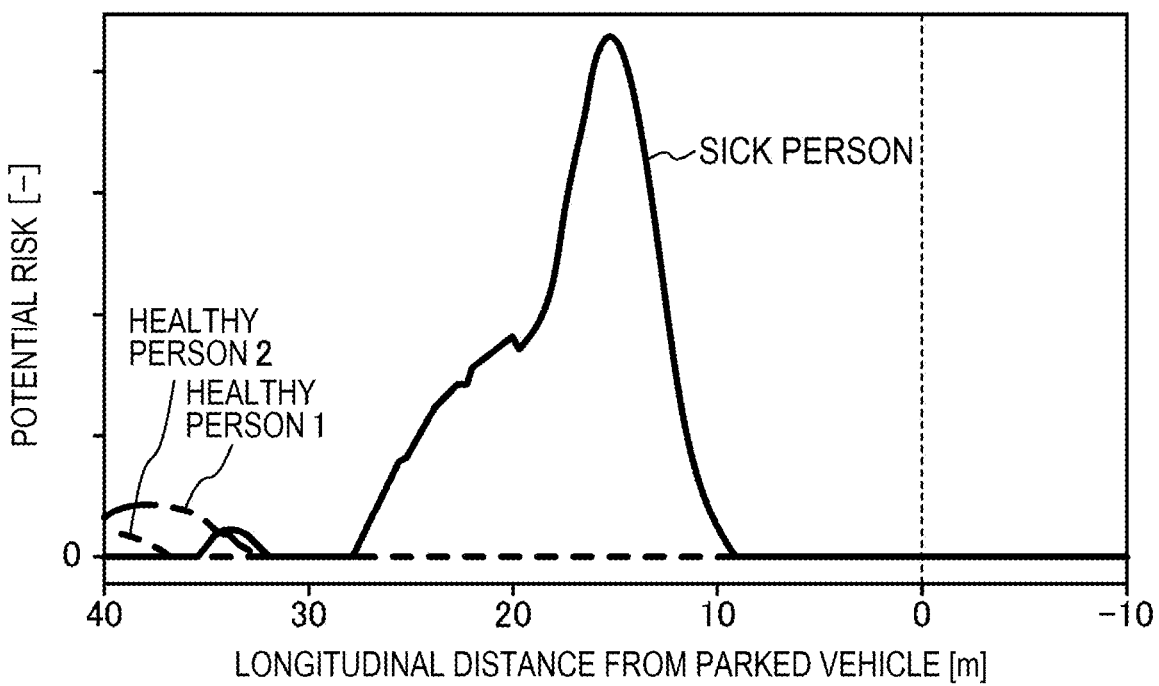

In FIG. 20, an example of the motion of the sightline during a normal time and an abnormal time in the case where the pedestrian shows up from a hidden position behind a vehicle is plotted. In FIG. 21, solid lines represent the motion of the sightline during the normal time, and broken lines represent the motion of the sightline during the abnormal time. During the normal time, the driver pays attention to the position where the pedestrian shows up several seconds (for example, two seconds) before the pedestrian actually shows up. Meanwhile, during the abnormal time, the driver pays attention to the road ahead and gazes at the pedestrian after the pedestrian shows up. In such a case, as illustrated in FIG. 22A, the sick person tends to approach an obstacle such as the parked vehicle in comparison with the healthy person, and thus the potential risk thereof is increased as illustrated in FIG. 22B. Thus, for example, the predictive function detection section 431 calculates a risk value corresponding to a distance between the host vehicle and the obstacle, and determines the driver abnormality based on the risk value.

Here, the predictive function detection section 431 may execute similar processing to the above-described "detection processing of the driving operation of the base function level". More specifically, for example, the predictive function detection section 431 generates a model parameter of the usual behavior of the driver's sightline. Then, from the driving operation information, the driving scene information, the vehicle behavior data, and the model parameter, the predictive function detection section 431 estimates the behavior of the driver's sightline in the normal state (the healthy state) in the driving scene of the moment. Then, the predictive function detection section 431 calculates an estimation error between the estimated sightline behavior and the actual sightline behavior, and outputs the estimation error to the abnormality determination section 440. Thereafter, the abnormality determination section 440 may determine that the driver has the sign of the abnormality based on whether the operation deviation degree received from the predictive function detection section 431 satisfies the specified criterion. As the model parameter, a general normal driver model may be used.

Abnormality Determination Processing

As described above, the target function levels in the periods T11, T13, T21, T25, T31, T33 in FIG. 4 are the predictive function level, the base function level, and the involuntary function level. Thus, in these periods, the abnormality determination section 440 determines whether the involuntary function level, which is output from the involuntary function detection section 420, the base function level, which is output from the base function detection section 435, and the predictive function level, which is output from the predictive function detection section 431, including the combination thereof match the specified condition. In this case, as illustrated in FIG. 14 described above, the combination of the indices may be determined according to the driving scene. Alternatively, the level value of each of the function levels may be scored or added, or the weighed average of such values may be calculated to set the specified condition for the total score including some or all of the scores selected from the base function level and the involuntary function level.

In addition, as described above, from the knowledge of the inventors, in the case where the driver suffers from the illness, the function related to the high-order action started being declined first, and thereafter, the decline in the function related to the base action and the decline in the function related to the involuntary action sequentially occur. Thus, as in the periods T11, T13, T21, T25, T31, T33, in the case where the plural target function levels are present (the predictive function level, the base function level, and the involuntary function model), and plural detection means can be used as in the case of "FOLLOWING TRAVEL" in FIG. 14, the abnormality determination section 440 may determine the abnormality by giving the priority to the output from the predictive function detection section 431. In addition, in the case where each of the plural function levels is scored, and the determination is made based on the total score (the combination), the output from the predictive function detection section 431 may be set to have the relatively higher score than the detection result of the other function levels.

As illustrated in FIG. 17, there is a case where the declining order of the function is known according to the type of the illness or the like. In such a case, the specified condition may be set stepwise in consideration of the declining order of the function. Then, the driver abnormality may be determined by determining whether the function matches the set condition. The declining order of the function may be stored as a table in the storage section 300 in advance.

For example, CASE A in FIG. 17 is a case where the base function declines after the predictive function has declined. An example that corresponds to such a case is that the driver suffers from the attention dysfunction due to infarction of the frontal cortex, which is progressed to impair the motor functions of the hands and the feet due to the infarction of the thalamus or the like. In such a case, the sightline behavior is possibly changed, and then unstable driving operation is possibly performed. In this case, the decline in the predictive function level related to the sightline behavior is detected. Thereafter, instability of the driving operation appears. That is, the decline in the base function level is detected. Accordingly, in consideration of this order, when the predictive function level related to the particular item declines to be equal to or lower than the specified determination threshold, the abnormality determination section 440 may lower the determination threshold of the base function level corresponding to the predictive function, to facilitate the abnormal determination of the involuntary function level. At this time, the determination threshold of the predictive function level and the determination threshold of the base function level are examples of the determination criteria.

For example, CASE C in FIG. 17 is a case where the involuntary function declines after the decline in the predictive function. An example that corresponds to such a case is a case where the driver suffers from the dysfunction due to the infarction of the frontal cortex, which is further progressed to cause the posture keeping difficult state (for example, of the unbalanced trunk, or the like) due to the infarction of the thalamus. In this case, the predictive function level of the sightline behavior is declined, and the unstable head behavior occurs thereafter, that is, the decline in the involuntary function level is detected. Accordingly, in consideration of this order, when the particular predictive function level is declined to be equal to or lower than the specified determination threshold, the abnormality determination section 440 may lower the determination threshold of the involuntary function level corresponding to the predictive function, to facilitate the abnormal determination of the involuntary function level. At this time, the determination threshold of the predictive function level and the determination threshold of the involuntary function level are examples of the determination criteria.

Abnormality Determination Processing

Figure 23:
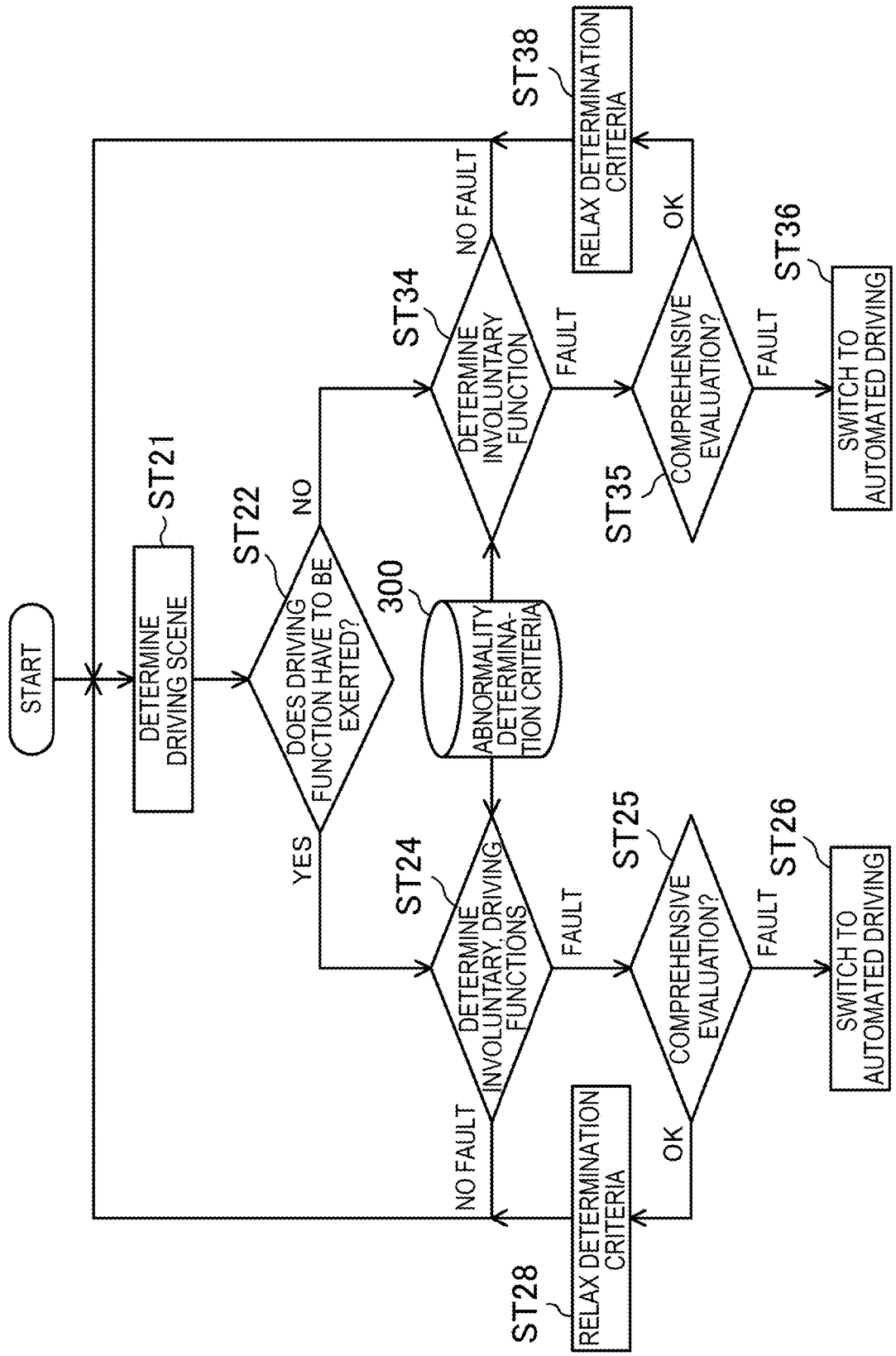
FIG. 23 is a flowchart illustrating determination operation of driver abnormality.

The description has been made so far on the driver abnormality determination processing by the vehicle controller 10 in a manner to be linked with the detection processing of each of the function levels. A description will herein be made on a series of driver abnormality determination operation with reference to FIG. 23 from a perspective of the driver abnormality determination. The block diagram, which will be used for the driver abnormality determination, is the same as that in the description so far and is FIG. 5, and the description on the configuration will not be repeated.

—Step ST21—

As described above, the driving scene recognition section 210 recognizes the driving scene of the vehicle based on the external environment information that is acquired by the external environment information acquisition device 60.

—Step ST22—

The calculation processing section 100 determines whether the driving scene, which is recognized by the driving scene recognition section 210, is a driving scene in which the driving function must be executed. Whether the driving scene is a driving scene in which the driving function must be executed can be determined from whether the driver performs the driving operation, for example, on the basis of the output of the driving operation sensor 66. The method for determining whether the driving scene is a driving scene in which the driving function must be executed is not particularly limited. For example, it may be determined from the travel state (stop state) of the vehicle based on the imaging result by the external camera 61 and the information from the vehicle state sensor 64 and the like. Alternatively, it may be determined by monitoring the driver state using the driver state sensor 67 such as the in-vehicle camera 68. Furthermore, those methods may be combined.

For example, in a case of the driving scene as illustrated in the period T11 in FIG. 4, the driving scene recognition section 210 determines that such a driving scene is the driving scene in which the driving function must be executed, that is, a driving scene in which the involuntary function, the base function, and the predictive function must be executed. As a result, it is determined "YES" in step ST22, and the processing flow proceeds to step "ST24". Note that this determination on the driving scene may be made by the recognition section 200 or may be made by the driver state estimation section 400.

—Step ST24—

The abnormality determination section 440 determines the driver abnormality by checking the results of the function levels of the driver, which are detected by the involuntary function detection section 420, the predictive function detection section 431, and the base function detection section 435, and the combination thereof with the specified conditions and the specified criteria. For example, as illustrated in FIG. 24, the determination criterion is provided for each of the functions of the involuntary function detection section 420, the predictive function detection section 431, and the base function detection section 435 (hereinafter also simply referred to as each of the functions). The abnormality determination section 440 determines whether each of the functions satisfies the respective determination criterion. FIG. 24 illustrates an example in which the determinations on the evaluation items, which have been described so far, are made.

FIG. 24 illustrates, as the exemplary evaluation items of the involuntary function, the periodicity characteristic amount (the head behavior) and the saccade amplitude (the sightline behavior). In an initial state (a state where the driver is normal), the determination criterion for the periodicity characteristic amount is based on the above-described determination line LTH (see FIG. 10). The determination criterion for the saccade amplitude is set such that, when a state where the saccade amplitude of the driver is less than 50% of the average for the normal driving by the driver continues for a specified time, it is determined that the saccade amplitude of the driver is abnormal. FIG. 24 illustrates, as the exemplary evaluation item of the base function, the steering operation deviation degree (the driving operation). The determination criterion for the steering operation deviation degree is set such that, when the estimation error is equal to or larger than 0.4 [deg], it is determined that the steering operation of the driver is abnormal (see FIG. 16). FIG. 24 illustrates, as the exemplary evaluation items of the predictive function, the saliency index (the sightline behavior) and the distance from the obstacle (the driving operation). In the case where an area, in which the saliency index exceeds 0.6, is equal to or larger than X (X is a positive number), it is determined that the sightline behavior of the driver is abnormal. Regarding the distance from the obstacle, when the risk value is equal to or higher than Y (Y is a positive value), it is determined that the driving operation of the driver is abnormal. These evaluation items and determination criteria are stored in the storage section 300, for example.

In the example illustrated in FIG. 24, in the period T11, all the items (functions) function normally. Accordingly, the abnormality determination section 440 determines that "no fault item" (described as "NO FAULT" in FIG. 23), and the processing flow returns to step S21.

For example, in the case of the period T11 in FIG. 4, the vehicle A travels on the town road. Thus, the driving scene thereof changes over time. In the case where it is assumed that the normal driver state continues in the period T11, the processing in ST21, ST22, and ST24 described above is repeatedly executed while an abnormality determination sensor, which is adopted according to the driving scene, is changed as needed.

—Step ST21—

When the processing flow returns to step ST21, the recognition result of the vehicle driving scene by the driving scene recognition section 210 is updated.

—Step ST22—

In FIG. 24, it is assumed that the next period T12 does not correspond to the driving scene in which the driving function must be executed, that is, in the next period T12, it is difficult to detect the driving function, and only the involuntary function is the determination target. In this case, it is determined "NO" in step ST22, and the processing flow proceeds to step ST34.

—Step ST34—

The abnormality determination section 440 determines whether there is the sign of the driver abnormality by checking the result of the function level of the driver, which is detected by the involuntary function detection section 420, and the combination of the measurement items for the involuntary function with the specified conditions and the specified criteria. In the example illustrated in FIG. 24, in the period T12, the saccade amplitude does not satisfy the determination criterion. As a result, in step ST34, it is determined that "fault item is present" (described as "FAULT" in FIG. 23), and the processing proceeds to next step ST35.

—Step ST35—

The abnormality determination section 440 integrates the measurement results by the involuntary function detection section 420 to determine the driver abnormality. That is, the abnormality determination section 440 determines whether the vehicle A should be switched to the automated driving. Here, for example, in the case where both of the items, which are the periodicity characteristic amount (the head behavior) and the saccade amplitude (the sightline behavior), are fault, the abnormality determination section 440 determines that the driver is abnormal (FAULT in step ST35), and switches to the automated driving (step ST36).

In the period T12 illustrated in FIG. 24, only the saccade amplitude is fault. Thus, it is determined "OK" in step ST35, and the processing flow proceeds to step ST38.

—Step ST38—

The abnormality determination section 440 relaxes the determination criteria, which are used to determine the driver abnormality, to facilitate the determination of the driver abnormality. That is, even in a state where the driver abnormality is not determined in a normal time, the driver abnormality is determined early. The determination criterion to be changed is not particularly limited. The determination criteria for the involuntary function may be changed, or the determination criteria for the driving function (the base function and/or the predictive function) may be changed. Here, (1) in regard to the predictive function, the evaluation criterion for the saliency index is relaxed from "fault at X or larger" to "fault at X−α (α is a positive number)", and (2) in regard to the base function, the steering operation deviation degree is relaxed from "fault at 0.4 [deg] or larger" to "fault at 0.35 [deg] or larger". When the processing in step ST38 is terminated, the processing flow returns to step ST21.

—Step ST21—

When the processing flow returns to step ST21, the recognition result of the vehicle driving scene by the driving scene recognition section 210 is updated. Here, it is assumed that the driving scene of the vehicle has been shifted to the period T13.

—Step ST22—

In FIG. 24, the period T13 corresponds to such a driving scene that the driving function must be executed. Thus, it is determined "YES" in step ST22, and the processing flow proceeds to step ST24.

—Step ST24—

As described above, the abnormality determination section 440 determines the driver abnormality based on the determination items and the determination criteria in FIG. 24. Here, the determination criterion for the saliency index has been relaxed. Then, in the period T13, it is determined fault in regard to the saliency index. Here, since the abnormality determination section 440 determines that the "fault item is present" (described as "FAULT" in FIG. 23), and the processing proceeds to next step ST25.

—Step ST25—

The abnormality determination section 440 integrates the evaluation results of the execution level of the involuntary function, which is detected by the involuntary function detection section 420, the execution level of the predictive function (the predictive function execution level), which is detected by the predictive function detection section 431, and the execution level of the base function (the base function execution level), which is detected by the base function detection section 435, and thereby determines the driver abnormality. That is, the abnormality determination section 440 determines whether the vehicle A should be switched to the automated driving. Here, for example, (1) in the case where both of the periodicity characteristic amount (the head behavior) and the saccade amplitude (the sightline behavior) in the involuntary function are fault or (2) in the case where the four or more evaluation items are fault, the abnormality determination section 440 determines that the driver is abnormal (FAULT in step ST25), and execute control to switch to the automated driving (step ST26).

In the example illustrated in FIG. 24, regarding the involuntary function, only the saccade amplitude is fault, which makes the two fault items among the evaluation items. Thus, it is determined "OK" in step ST25, and the processing flow proceeds to step ST28.

—Step ST28—

The abnormality determination section 440 relaxes the determination criteria, which are used to determine the driver abnormality, to facilitate the determination of the driver abnormality. That is, even in the state where the driver abnormality is not determined in the normal time, the driver abnormality is determined early. The determination criterion to be changed is not particularly limited. The determination criteria for the execution level of the involuntary function may be changed, or the determination criteria for the execution level of the driving function (the base function and/or the predictive function) may be changed. Here, in addition to the relaxation of the conditions in step ST38 described above, (1) in regard to the execution level of the base function, the steering operation deviation degree is further relaxed from "fault at 0.35 [deg] or larger" to "fault at 0.3 [deg] or larger", and (2) in regard to the execution level of the predictive function, the evaluation criterion for the distance from the obstacle is relaxed from "fault with the risk value being Y or higher" to "fault with the risk value being Y−β (β is a positive number) or higher". When the processing in step ST28 is terminated, the processing flow returns to step ST21.

—Step ST21—

When the processing flow returns to step ST21, the recognition result of the vehicle driving scene by the driving scene recognition section 210 is updated. It is assumed that the driving scene of the vehicle remains in the period T13.

—Step ST22—

The period T13 corresponds to such a driving scene that the driving function must be continuously executed. Thus, it is determined "YES" in step ST22, and the processing flow proceeds to step ST24.

—Step ST24—

As described above, the abnormality determination section 440 determines the driver abnormality based on the determination items and the determination criteria in FIG. 24. Here, it is continuously determined that the "fault item is present", and the processing flow proceeds to next step ST25.

—Step ST25—

As described above, the abnormality determination section 440 integrates the evaluation results of the execution level of the involuntary function, the execution level of the predictive function, and the execution level of the base function to determine the driver abnormality. Here, it is assumed that the fault evaluation items are increased to four (see the rightmost column in FIG. 24). In this case, it is determined "FAULT" in step ST25, and the processing flow proceeds to step ST26.

—Step ST26—

The abnormality determination section 440 instructs the travel control section 500 to make the vehicle automatically evacuate to an evacuation position (for example, the road shoulder) for the stop. As a result, the vehicle A is controlled by the travel control section 500, makes evacuation travel to the road shoulder, and stops at the evacuation position.

As it has been described so far, according to this embodiment, the calculation processing section 100 is configured to include: the involuntary function detection section 420 that detects the execution level of the involuntary function of the driver on the basis of the detection data by the driver state sensor for detecting the driver state (including the driver state sensor 67 in the embodiment); the driving function detection section 430 that detects the execution level of the driving function of the driver on the basis of the detection data by the driving operation sensor for detecting the driving operation by the driver (including the driving operation sensor 66 in the embodiment) in the case where the driver performs the driving operation; and the abnormality determination section 440 that determines the driver abnormality on the basis of the execution level of the involuntary function, which is detected by the involuntary function detection section 420, and the execution level of the driving function, which is detected by the driving function detection section 430.

Then, in the case where the involuntary function detection section 420 detects that the execution level of the involuntary function no longer satisfies the determination criteria, the abnormality determination section 440 relaxes the determination criteria for the execution level of the driving function by the driving function detection section 430 to facilitate the determination of the driver abnormality.

The calculation processing section 100 is configured to include the involuntary function detection section 420 and the driving function detection section 430 as described in the above paragraph. In such a configuration, in the case where it is detected that one function level of the involuntary function level, which is detected by the involuntary function detection section 420, and the driving function level, which is detected by the driving function detection section 430, has declined to be equal to or lower than the specified determination criteria, the abnormality determination section 440 may relax the determination criteria for the other function level so as to facilitate the determination of the driver abnormality.

When the configuration as described in the above two paragraphs is adopted, it is possible to simultaneously determine the driver abnormality early and improve the accuracy of the determination of the driver abnormality by combining the detection results by the involuntary function detection section 420 and the driving function detection section 430. The involuntary function detection section 420 is characterized that the involuntary function detection section 420 can always make measurement regardless of the driving scene but cannot always make the clear determination on the driver. The driving function detection section 430 has the indices that can only be used when the driving operation is performed, but is high in the detection accuracy of the driver abnormality.

The following description relates to a computer environment in which embodiments of the present disclosure may be implemented. This environment may include an embedded computer environment, local multi-processor embodiment, remote (e.g., cloud-based) environment, or a mixture of all the environments.

Figure 25:
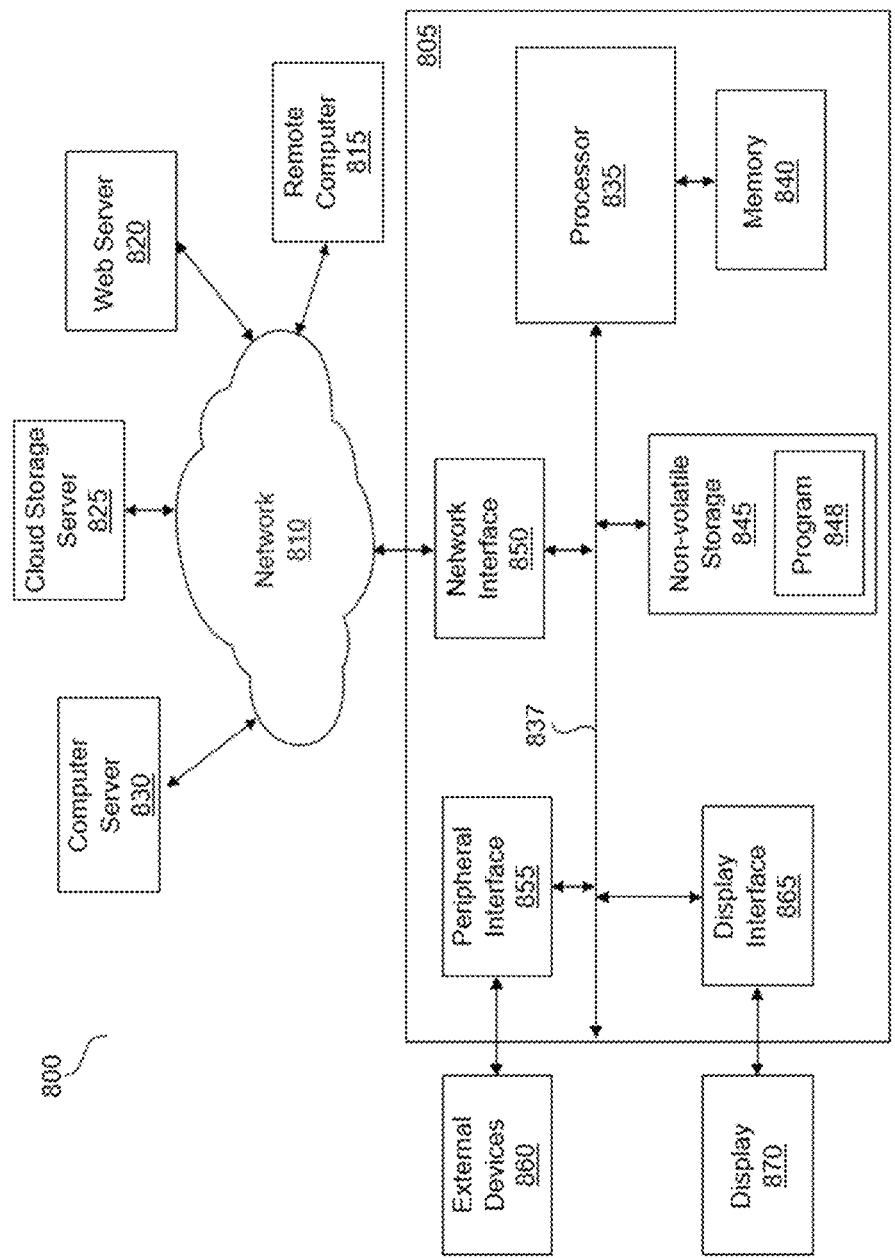
FIG. 25 is a block diagram of computer-based circuitry that may be used to implement control features of the present disclosure.

FIG. 25 illustrates a block diagram of a computer that may implement the various embodiments described herein. The present disclosure may be embodied as a system, a method, and/or a computer program product. The computer program product may include a computer readable storage medium on which computer readable program instructions are recorded that may cause one or more processors to carry out aspects of the embodiment.

The non-transitory computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, Python, R, C, C++, C# or similar programming languages. The computer readable program instructions may execute entirely on a user's personal computer, notebook computer, tablet, or smartphone, entirely on a remote computer or compute server, or any combination of these computing devices. The remote computer or compute server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 25 is a functional block diagram illustrating a networked system 800 of one or more networked computers and servers. In an embodiment, the hardware and software environment illustrated in FIG. 25 may provide an exemplary platform for implementation of the software and/or methods according to the present disclosure.

Referring to FIG. 25, a networked system 800 may include, but is not limited to, computer 805, network 810, remote computer 815, web server 820, cloud storage server 825 and computer server 830. In some embodiments, multiple instances of one or more of the functional blocks illustrated in FIG. 25 may be employed.

Additional detail of computer 805 is shown in FIG. 25. The functional blocks illustrated within computer 805 are provided only to establish exemplary functionality and are not intended to be exhaustive. And while details are not provided for remote computer 815, web server 820, cloud storage server 825 and compute server 830, these other computers and devices may include similar functionality to that shown for computer 805.

Computer 805 may be built into the automobile, a personal computer (PC), a desktop computer, laptop computer, tablet computer, netbook computer, a personal digital assistant (PDA), a smart phone, or any other programmable electronic device capable of communicating with other devices on network 810.

Computer 805 may include processor 835, bus 837, memory 840, non-volatile storage 845, network interface 850, peripheral interface 855 and display interface 865. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 835 may be one or more single or multi-chip microprocessors, such as those designed and/or manufactured by Intel Corporation, Advanced Micro Devices, Inc. (AMD), Arm Holdings (Arm), Apple Computer, etc. Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 837 may be a proprietary or industry standard high-speed parallel or serial peripheral interconnect bus, such as ISA, PCI, PCI Express (PCI-e), AGP, and the like.

Memory 840 and non-volatile storage 845 may be computer-readable storage media. Memory 840 may include any suitable volatile storage devices such as Dynamic Random Access Memory (DRAM) and Static Random Access Memory (SRAM). Non-volatile storage 845 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 848 may be a collection of machine readable instructions and/or data that is stored in non-volatile storage 845 and is used to create, manage and control certain software functions that are discussed in detail elsewhere in the present disclosure and illustrated in the drawings. In some embodiments, memory 840 may be considerably faster than non-volatile storage 845. In such embodiments, program 848 may be transferred from non-volatile storage 845 to memory 840 prior to execution by processor 835.

Computer 805 may be capable of communicating and interacting with other computers via network 810 through network interface 850. Network 810 may be, for example, a local area network (LAN), a wide area network (WAN) such as the Internet, or a combination of the two, and may include wired, wireless, or fiber optic connections. In general, network 810 can be any combination of connections and protocols that support communications between two or more computers and related devices.

Peripheral interface 855 may allow for input and output of data with other devices that may be connected locally with computer 805. For example, peripheral interface 855 may provide a connection to external devices 860. External devices 860 may include input devices, e.g., any or all of the devices in the information acquisition means 10 and/or other suitable input devices, and output devices, e.g., any or all of the various actuator devices AC and/or other suitable output devices, e.g., a speaker. External devices 860 may also include portable computer-readable storage media such as, for example, thumb drives, portable optical or magnetic disks, and memory cards. Software and data used to practice embodiments of the present disclosure, for example, program 848, may be stored on such portable computer-readable storage media. In such embodiments, software may be loaded onto non-volatile storage 845 or, alternatively, directly into memory 840 via peripheral interface 855. Peripheral interface 855 may use an industry standard connection, such as RS-232 or Universal Serial Bus (USB), to connect with external devices 860.

Display interface 865 may connect computer 805 to display 870, e.g., a head-up display or a screen of a car navigation system. Display 870 may be used, in some embodiments, to present a command line or graphical user interface to a user of computer 805. Display interface 865 may connect to display 870 using one or more proprietary or industry standard connections, such as VGA, DVI, DisplayPort and HDMI.

As described above, network interface 850, provides for communications with other computing and storage systems or devices external to computer 805. Software programs and data discussed herein may be downloaded from, for example, remote computer 815, web server 820, cloud storage server 825 and compute server 830 to non-volatile storage 845 through network interface 850 and network 810. Furthermore, the systems and methods described in this disclosure may be executed by one or more computers connected to computer 805 through network interface 850 and network 810. For example, in some embodiments the systems and methods described in this disclosure may be executed by remote computer 815, computer server 830, or a combination of the interconnected computers on network 810.

Data, datasets and/or databases employed in embodiments of the systems and methods described in this disclosure may be stored and or downloaded from remote computer 815, web server 820, cloud storage server 825 and compute server 830.

DESCRIPTION OF REFERENCE SIGNS AND NUMERALS

A: vehicle
10: Vehicle controller (driver abnormality determination apparatus)
66: Driving operation sensor
67: Driver state sensor
420: Involuntary function detection section
431: Predictive function detection section
435: Base function detection section
440: Abnormality determination section
800: Networked system
805: Computer
810: Network
815: Remote computer
820: Web Server
825: Cloud storage server
830: Computer server
835: Processor
837: Bus
840: Memory
845: Non-volatile storage
848: Program
850: Network interface (wireless)
855: Peripheral Interface
860: External devices
865: Display interface
870: Display

The invention claimed is:

1. A driver abnormality determination apparatus for a vehicle, the driver abnormality determination apparatus comprising:
circuitry configured to detect a driving operation of a driver;
detect a driver state of the driver;
detect an execution level of an involuntary function of the driver based on the driver state;
detect an execution level of a driving function of the driver based on the driving operation of the driver; and
determine a driver abnormality based on the execution level of the involuntary function and the execution level of the driving function, wherein
on condition that a function level of one of the execution level of the involuntary function and the execution level of the driving function is equal to or lower than a specified determination criterion, the circuitry is configured to relax a determination criterion for the other function level, and
to detect the execution level of the driving function, the circuitry is configured to detect:

an execution level of a predictive function related to a predictive function of the driver; and an execution level of a base function related to a base function that serves as basis of the driving operation by the driver, and on condition that the execution level of the predictive function is equal to or lower than a specified determination criterion, relax the determination criterion for the execution level of the base function.

2. The driver abnormality determination apparatus according to claim 1, wherein, on condition that the execution level of the involuntary function is equal to or lower than the specified determination criterion, the circuitry is configured to relax the determination criterion for the execution level of the driving function.

3. The driver abnormality determination apparatus according to claim 1, wherein, to detect the execution level of the involuntary function, the circuitry is configured to perform at least one of:

detect a motor function level of a right foot of the driver based on data from an accelerator pedal position sensor; and/or detect a motor function level of a right hand and/or a left hand of the driver based on data from a steering angle sensor, wherein the motor function level indicates a degree that the motor function is executed normally.

4. The driver abnormality determination apparatus according to claim 1, wherein, to detect the execution level of the base function, the circuitry is configured to detect at least one of:

the driving operation of the driver;
behavior of the driver's sightline; and/or
behavior of the driver's head.

5. The driver abnormality determination apparatus according to claim 1, wherein, to detect the execution level of the predictive function, the circuitry is configured to detect at least one of:

the driving operation of the driver;
behavior of the driver's sightline; and/or
behavior of the driver's head.

6. The driver abnormality determination apparatus according to claim 1, wherein, to detect the execution level of the involuntary function, the circuitry is configured to detect at least one of:

a motor function level of a pupillary reflex by calculating microsaccades;

a motor function level of the pupillary reflex by calculating an amount of nystagmus; and/or an autonomic function level of a sympathetic nerve/a parasympathetic nerve of the driver by calculating turning of the eyeballs, wherein the motor function level indicates a degree that the motor function is executed normally.

7. The driver abnormality determination apparatus according to claim 1, wherein, to detect the execution level of the involuntary function, the circuitry is configured to detect at least one of:

an autonomic function level of a sympathetic nerve/a parasympathetic nerve of the driver by calculating autocorrelation of behavior of the driver's head;

a vestibular function level of a vestibulo-ocular reflex of the driver by calculating cross-correlation between the head and the driver's sightline based on the behavior of the driver's head and behavior of the driver's sightline; and/or the autonomic function level of the sympathetic nerve/the parasympathetic nerve of the driver by calculating cross-correlation between the behavior of the driver's head and an external force.

8. A driver abnormality determination method for a driver in a vehicle, the method comprising:

detecting a driving operation of a driver;
detecting a driver state of the driver;
detecting an execution level of an involuntary function of the driver based on the driver state;
detecting an execution level of a driving function of the driver based on the driving operation of the driver;
determining a driver abnormality based on the execution level of the involuntary function and the execution level of the driving function; and
comparing a function level of one of the execution level of the involuntary function and the execution level of the driving function to a specified determination criterion, wherein
in response to the function level of one of the execution level of the involuntary function and the execution level of the driving function being equal to or lower than the specified determination criterion, relaxing a determination criterion for the other function level, and
detecting the execution level of the driving function, includes:
detecting an execution level of a predictive function related to a predictive driving function of the driver;
detecting an execution level of a base function related to a base function that serves as basis of the driving operation by the driver, and
on condition that the execution level of the predictive function is equal to or lower than a specified determination criterion, relaxing the determination criterion for the execution level of the base function.

9. A non-transitory computer readable storage including computer readable instructions that when executed by a controller cause the controller to execute a driver abnormality determination method for a driver in a vehicle, the method comprising:

detecting a driving operation of a driver;
detecting a driver state of the driver;
detecting an execution level of an involuntary function of the driver based on the driver state;
detecting an execution level of a driving function of the driver based on the driving operation of the driver; and
determining a driver abnormality based on the execution level of the involuntary function and the execution level of the driving function, wherein
on condition that a function level of one of the execution level of the involuntary function and the execution level of the driving function is equal to or lower than a specified determination criterion, relaxing a determination criterion for the other function level, and
detecting the execution level of the driving function, includes:
detecting an execution level of a predictive function related to a predictive driving function of the driver;
detecting an execution level of a base function related to a base function that serves as basis of the driving operation by the driver, and
on condition that the execution level of the predictive function is equal to or lower than a specified determination criterion, relaxing the determination criterion for the execution level of the base function.

* * * * *